US006265558B1

(12) United States Patent
Cook et al.

(10) Patent No.: US 6,265,558 B1
(45) Date of Patent: *Jul. 24, 2001

(54) THIOL-DERIVATIZED NUCLEOSIDES AND OLIGONUCLEOSIDES

(75) Inventors: Phillip Dan Cook, Fallbrook; Muthiah Manoharan, Carlsbad, both of CA (US)

(73) Assignee: ISIS Pharmaceuticals, Inc., Carlsbad, CA (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/383,856

(22) Filed: Aug. 26, 1999

Related U.S. Application Data

(62) Continuation of application No. 08/924,326, filed on Sep. 5, 1997, now Pat. No. 6,114,513, which is a continuation of application No. 08/458,396, filed on Jun. 2, 1995, now Pat. No. 5,852,182, which is a continuation-in-part of application No. 08/116,801, filed on Sep. 3, 1993, which is a continuation-in-part of application No. 08/211,882, filed as application No. PCT/US92/09196 on Oct. 23, 1992, now Pat. No. 5,578,718, application No. 09/383,856, filed on Aug. 26, 1999, which is a continuation-in-part of application No. 07/782,374, filed on Oct. 24, 1991, now abandoned, which is a continuation-in-part of application No. 07/463,358, filed on Jan. 11, 1990, now abandoned, and a continuation-in-part of application No. 07/566,977, filed on Aug. 13, 1990, now abandoned.

(51) Int. Cl.$^7$ ............................. C07H 21/02; C07H 21/04
(52) U.S. Cl. .................... 536/23.1; 536/22.1; 536/24.31; 536/25.3; 536/25.32; 536/27.6; 536/27.8; 536/27.81; 536/281; 536/28.4; 536/28.5
(58) Field of Search .................. 536/23.1, 22.1, 536/24.31, 25.3, 25.32, 27.6, 27.8, 27.81, 28.1, 28.4, 28.5; 530/395

(56) References Cited

U.S. PATENT DOCUMENTS

| | | | |
|---|---|---|---|
| 3,687,808 | * | 8/1972 | Merigan et al. . |
| 4,381,344 | | 4/1983 | Rideout et al. ........................ 455/87 |
| 4,511,713 | * | 4/1985 | Miller et al. . |
| 4,689,320 | * | 8/1987 | Kaii . |
| 4,760,017 | * | 7/1988 | McCormick . |
| 4,876,335 | * | 10/1989 | Yamane et al. . |
| 4,910,300 | | 3/1990 | Urdea et al. ........................ 536/287 |
| 4,958,013 | | 9/1990 | Letsinger . |
| 4,965,350 | * | 10/1990 | Inoue et al. . |
| 5,015,733 | | 5/1991 | Smith et al. ............................ 536/23 |
| 5,108,921 | | 4/1992 | Low et al. ........................ 435/240.1 |
| 5,466,786 | | 11/1995 | Buhr et al. ........................ 536/26.26 |
| 5,470,967 | | 11/1995 | Huie et al. ........................ 536/24.3 |
| 5,578,718 | | 11/1996 | Cook et al. ........................ 536/27.21 |

FOREIGN PATENT DOCUMENTS

| | | | |
|---|---|---|---|
| 0251283 | | 1/1988 | (EP) . |
| 0 407 816 A | * | 1/1991 | (EP) . |
| 0 423 839 A | * | 4/1991 | (EP) . |
| WO 86/02929 | | 5/1986 | (WO) . |
| WO 89/02931 | | 4/1989 | (WO) . |
| WO 90/10448 | | 9/1990 | (WO) . |
| WO 91/00243 | | 1/1991 | (WO) . |
| WO 91 06556 A | * | 5/1991 | (WO) . |
| WO 91 10671 A | * | 7/1991 | (WO) . |
| WO 91/15500 | | 10/1991 | (WO) . |
| WO 91/14696 | | 11/1991 | (WO) . |
| WO 93 07883 A | * | 4/1993 | (WO) . |
| WO 92/05186 | | 4/1993 | (WO) . |

OTHER PUBLICATIONS

Asseline, U. et al.,"Solid–Phase Preparation of 5'–3'–Heterobifunctional Oligodeoxyribonucleotides Using Modified Solid Supports," *Tetrahedron* 1992, 48, 1233–1254.

Asseline, U. et al., "Nucleic acid–binding molecules with high affinity and base sequence specificity: Intercalating agents covalently linked to oligodeoxynucleotides," *Proc. Natl. Acad. Sci. USA* 1984, 81, 3297–3301.

Atherton,E. et al., *The Peptides*, Gross and Meienhofer, Eds, Academic Press; New York, vol. 9:1–38, 1983.

Baker, B.F., "Decapitation of a 5'–Capped Oligoribonucleotide by o–Phenanthroline: CU(II)," *J. Am. Chem. Soc.* 1993, 115, 3378–3379.

Beaucage, S. et al., "Advances in the Synthesis of Oligonucleotides by the Phosphoramidite Approach," *Tetrahedron* 1992, 48, 2223–2211.

Bennett, C.F. et al.,"Cationic Lipids Enhance Cellular Uptake and Activity of Phosphorothioate Antisense Oligonucleotides", *Molecular Pharmacology* 1991, 41, 1023–1033.

Betebenner, D.A., et al., "Hepatobiliary Delivery of Polyaminopolycarboxylate Chelates: Synthesis and Characterization of a Cholic Acid Conjugate of EDTA and Biodistribution adn Imaging Studies with Its Indium–111 Chelate", *Bioconjugate Chem.* 1991, 2, 117–123.

Bischoff, R. et al., "Introduction of 5'–Terminal Functional Groups into Synthetic Oligonucleotides for Selective Immobilization," *Analy. Biochem.* 1987, 164, 336–344.

Blackburn, G. et al., "Studies in Phosphorylation. Part XXIX. The Synthesis of Dialkyl Phosphates from Monoalkyl Phosphonates: Direct Oxidative Esterification", *J. Chem. Soc.* 1966, 239–245.

Primary Examiner—James O. Wilson
(74) Attorney, Agent, or Firm—Woodcock Washburn Kurtz Mackiewicz & Norris LLP

(57) ABSTRACT

Nucleosides and linked nucleosides functionalized to include alkylthiol chemical functionality at ribofuranosyl positions, nucleosidic base positions, or on internucleoside linkages. In certain embodiments, the compounds of the invention further include steroids, reporter molecules, reporter enzymes, lipophilic molecules, peptides or proteins attached to the nucleosides through the alkylthio group.

13 Claims, No Drawings

OTHER PUBLICATIONS

Chiang, M.-Y. et al., "Antisense Oligonucleotides Inhibit Intercellular Adhesion Molecule 1 Expression by Two Distinct Mechanisms", *J. of Biol. Chem.* 1991, 266, 18162–18171.

Chollet, A., "Selective Attachment of Oligonucleotides to Interleukin–1 beta and Targeted Delivery to Cells", *Nucleosides & Nucleotides* 1990, 9, 957–966.

Cohen, J. in *Oligonucleotides: Antisense Inhibitors of Gene Expression*, CRC Press, Inc., Boca Raton, FL, pp. 1–255, 1989.

Corey, D. et al., "Sequence–Selective Hydrolysis of Duplex DNA by an Oligonucleotide–Directed Nuclease", *J. Am. Chem. Soc.* 1989, 111, 8523–8525.

Corey, D. et al., "Generation of a Hybrid Sequence–Specific Single–Stranded Deoxyribonuclease", *Science*, 1987, 238, 1401–1403.

Damha, M. et al., "An Improved Procedure for Derivatization of Controlled–Pore Glass Beads for Solid–Phase Oligonucleotide Synthesis", *Nuc. Acids Res.* 1990, 18, 3813–3821.

Delgado, C. et al., "The Uses and Properties of PEG–Linked Proteins", *Critical Reviews in Therapeutic Drug Carrier Systems*, 1992, 9, 249–304.

Dingwall, C., et al., "Protein Import Into the Cell Nucleus", *Ann. Rev. Cell Biol.*, 1986, 2, 367–90.

DiZio, J. et al., "Progestin–Thenium Complexes: Metal–Labeled Steroids with High Receptor Binding Affinity, Potential Receptor–Directed Agents for Diagnostic of Therapy", *Bioconjugate Chem.* 1991, 2, 353–366.

Dreyer, G. et al., "Sequence–Specific Cleavage of Single–Stranded DNA: Oligodeoxynucleotide–EDTA.Fe(II)", *PNAS USA* 1985, 82, 968–972.

Egholm, M. et al.,"Peptide Nucleic Acids (PNA). Oligonucleotide Analogues with an Achiral Peptide Backbone",*J. Am. Chem. Soc.* 1992, 114, 1895–1897.

Ferentz, A.E. and Verdine, G.L., "Disulfide Cross–Linked Oligonucleotides", *J. Am. Chem. Soc.* 1991, 113, 4000–4002.

Fidanza, J. et al., "Site–Specific Labeling of DNA Sequences Containing Phosphorothioate Diesters", *J. Am. Chem. Soc.* 1992, 114, 5509–5517.

Fidanza, J. et al., "Use of a Thiol Tether for the Site–Specific Attachment of Reporter Groups of DNA", *J. Org. Chem.* 1992, 57, 2340–2346.

Froehler, B. et al., "Synthesis of DNA via Deoxynucleotide H–Phosphonate Intermediates", *Nucleic Acids Research* 1986, 14, 5399–5407.

Gaur, R. et al., "A Simple Method for the Introduction of Thiol Group at 5'–Termini or Oligodeoxynucleotides", *Nuc. Acids Res.* 1989, 17, 4404.

Greene et al., *Protective Groups in Organic Synthesis*, 2d edition, New York, John Wiley & Sons, pp. 178–223, 1991.

Greenfield, L. et al., "Thiol–Containing Cross–Linking Agent with Enhanced Steric Hindrance", *Biodonjugate Chem.* 1990, 1, 400–410.

Guerra, F.I. et al., "Synthetic 7–Glucosyl Phospholipid as a Drug Transport System", *Tetrahedron Letters* 1987, 28, 3581–3584.

Haralambidis J., et al., "Preparation of Base–modified Nucleosides Suitable for Non–Radioactive Label Attachment and Their Incorporation Into Synthetic Oligodeoxyribonucleotides", *Nucleic Acids Research* 1987, 15, 4857–4876.

Haralambidis, J. et al., "The Solid Phase Synthesis of Oligonucleotides containing a 3'–Peptide Moiety", *Tetrahedron Letters* 1987, 28, 5199–5202.

Harris, C. et al., "New Strategy for the Synthesi of Oligodeoxynucleotides Bearing Adducts at Exocyclic Amino Sites of Purine Nucleosides", *J. Am. Chem. Soc.* 1991, 113, 4328–4329.

Iyer, R. et al., "3H–1, 2–Benzodithiole–3–one, 1,1–Dioxide as an Imrpoved Sulfurizing Reagent in the Solid–Phase Synthesis of Oligodeoxyribonucleoside Phosphorothioates", *J. Am. Chem. Soc.* 1990, 112, 1253–1254.

Jablonski, E. et al.,"Preparation of Oligodeoxynucleotide–Alkaline Phosphatase Conjugates and Their Use as Hybridization Probes", *Nucleic Acid Research* 1986, 14, 6115–28.

Juby, C.D., et al., "Facile Preparation of 3'Oligonucleotide–Peptide Conjugates", *Tetrahedron Letters* 1991, 32, 879–882.

Krieg, A.M., et al., "Uptake of Oligodeoxyribonucleo–tides by Lymphoid Cells Is Heterogeneous and Inducible", *Antisense Research and Development* 1991 1, 161–171.

Lemaitre, M. et al., "Specific Antiviral Activity of a Poly(L–lysine)–Conjugated Oligodeoxyribonucleotide Sequence Complementary to Vesicular Stomatitis Virus N Protein mRNA Initiation Site", *PNAS USA* 1987, 84, 648–652.

Leonetti, J.P. et al., "Biological Activity of Oligonucleotide–Poly(L–lysine) Conjugates: Mechanism of Cell Uptake", *Bioconjugate Chem.* 1990, 1, 149–153.

Letsinger, R.L., et al., "Cholesteryl–Conjugated Oligonucleotides: Synthesis, Properties, and Activity as Inhibitors of Replication of Human Immunodeficiency Virus in Cell Culture", *Proc. Natl. Acad. Sci. USA* 1989, 86, 6553–6556.

MacMillan, A. et al., "Synthesis of Functionally Tethered Oligodeoxynucleotides by the Convertible Nucleoside Approach", *J. Org. Chem.* 1990, 55, 5931–5933.

Manoharan, M. et al., "Novel Functionalization of the Sugar Moiety of Nucleic Acids For Multiple Labeling in the Minor Groove", *Tetrahedron Letters*, 1991, 32, 7171–7174.

Meyer, R. et al., "Efficient, Specific Cross–Linking and Cleavage of DNA by Stable, Synthetic Complementary Oligodeoxynucleotides", *J. Am. Chem. Soc.* 1989, 111, 8517–8519.

Miller, P.S. et al., "A New Approach to Chemotherapy Based on Molecular Biology and Nucleic Acid Chemistry: Matagen: Masking Tape for Gene Expression", *Anti–Cancer Drug Design* 1987, 2, 117–128.

Mirabelli, C.K. et al., "In vitro and in vivo pharmacologic activities of antisense oligonucleotides", *Anti–Cancer Drug Design* 1991, 6, 647–661.

Mori, K. et al., "Synthesis and Properties of Novel 5'–Linked Oligos", *Nucleosides & Nucleotides* 1989, 8, 649–657.

Nelson, P. et al., "Bifunctional Oligonucleotide Probes Synthesized Using a Novel CPG Support Are Able to Detect Single Base Pair Mutants", *Nuc. Acids Res.* 1989, 17, 7187–7194.

Ouchi, T. et al., "Synthesis and Antitumor Activity of Poly(Ethylene Glycol)s Linked to 5–Fluorouracil Via a Urethan or Urea Bond", *Drug Design and Discovery* 1992, 9, 93–105.

Pidgeon, C. et al., "Synthesis and Liposome Encapsulation of Antisense Oligonucleotide–Intercalator Conjugates", *Annals New York Academy of Sciences*, pp. 593–596.

Ramirez, F. et al., "Nucleotidophospholipids: Oligonucleotide Derivatives with Membrane–Recognition Groups", *J. Am. Chem. Soc.* 1982, 104, 5483–5486.

Ravasio, N. et al., "Selective Hydrogenations Promoted by Copper Catalysts. 1. Chemoselectivity, Regioselectivity, and Stereoselectivity in the Hydrogenation of 3–Substituted Steroids", *J. Org. Chem.* 1991, 56, 4329–4333.

Shea, R. et al., "Synthesis, Hybridization Properties and Antiviral Activity of Lipid–Oligodeoxynucleotide Conjugates", *Nuc. Acids Res.* 1990, 18, 3777–3783.

Sigman, D.S., "Chemical Nucleases", *Biochemistry*, 1990, 29, 9097–9105.

Sinha, N.D. et al., "The Preparation and Application of Functionalized Synthetic Oligonucleotides: III. Use of H–Phosphonate Derivatives of Protected Amino–Hexanol and Mercapto–Propanol or –Hexanol", *Nucleic Acids Res.* 1988, 16, 2659–2669.

Sluka, J. et al., "Reagents and Methods for the Solid–Phase Synthesis of Protein–EDTA for Use in Affinity Cleaving", *J. Am. Chem. Soc.* 1990, 112, 6369–6374.

Smith–Jones, P. et al., "Antibody Labeling with Copper–67 Using the Bifunctional Marcrocycle 4–((1,4,8,11–Tetraazacyclotetradec–1–yl)methyl) Benzoic Acid", *Bioconjugate Chem.* 1991, 2, 415–421.

Solomons, T.W. et al., *Organic Chemistry*, John Wiley & Sons, New York, pp. 818–819, 1980.

Sproat, B. et al., "The Synthesis of Protected 5'-Mercapto-2', 5'-Dideoxyribonucleoside-3'-O-Phosphoramidites; Uses of 5'-Mercapto-Oligodeoxyribonucleotides", *Nucleic Acids Res.* 1987, 15, 4837–4848.

Stein, C. et al., "Antisense Oligonucleotides as Therapeutic Agents—Is the Bullet Really Magical?" *Science* 1993, 261, 1004–1012.

Telser, J. et al., "Synthesis and Characterization of DNA Oligomers and Duplexes Containing Covalently Attached Molecular Labels: Comparison of Biotin, Fluorescin, and Pyrene Labels by Thermodynamic and Optical Spectroscopic Measurements", *J. Am. Chem. Soc.* 1989, 111, 6966–6976.

Tseng, B. et al.,"Antisense Oligonucleotide Technology in the Development of Cancer Therapeutics", *Cancer Gene Therapy* 1994, 1(1), 65–71.

Uhlmann, E. and A. Peyman, "Antisense Oligonucleotides: A New Therapeutic Principle," *Chem. Rev.* 1990, 90, 543–584.

Vasseur, J. et al., "Oligonucleosides: Synthesis of a Novel Methylhydroxylamine–Linked Nucleosides Dimer and its Incorporation into Antisense Sequences", *J. Am. Chem. Soc.* 1992, 114, 4006–4007.

Veber, D. et al., "Isonicotinyloxycarbonyl, a Novel Amino Protecting Group for Peptide Synthesis", *J. Org. Chem.* 1977, 42, 3286–3288.

Wagner, D. et al.,"Preparation and Synthetic Utility of Some Organotin Derivatives of Nucleosides", *J. Org. Chem.* 1974, 39, 24–30.

Wychowski, C. et al., "The Intranuclear Location of Simian Virus 40 Polypeptides VP2 and VP3 Depends on a Specific Amino Acid Sequence", *J. Virol.* 1987, 61, 3862–3869.

Yamana, K. et al., "Synthesis of Oligonucleotide Derivatives with Pyrene Group at Sugar Fragment", *Tetrahedron Lett.* 1991, 32, 6347–6350.

Yamana, K. et al., "Synthesis and Interactive Properties of an Oligonucleotide with Anthraquinone at the Sugar Fragment", *Bioconjugate Chem.* 1990, 1, 319–324.

Yoneda, Y. et al., "Synthetic Peptides Containing a Region of SV40 Large T–Antigen Involved in Nuclear Localization Direct the Transport of Proteins Into the Nucleus", *Experimental Cell Research* 1987, 170, 439.

Zhang, Z. and McCormick, "Uptake of N–(4'–pyridoxyl)amines and Release of Amines by Renal Cells: A Model for Transporter–Enhanced Delivery of Bioactive Compounds", *PNAS USA* 1991, 88, 10407–10410.

Zuckermann, R. et al., "Site–Selective Cleavage of RNA by a Hybrid Enzyme", *J. Am. Chem. Soc.* 1988, 110, 1614–1615.

Zuckermann et al., "Efficient Methods for Attachment of Thiol Specific Probes to The 3'–Ends of Synthetic Oligodeoxyribonucleotides", *Nucleic Acids Research* 1987, 15, 5305–5320.

Studer, et al., "One–Step Synthesis of Mono–N–substituted Azamacrocycles with a Carboxylic Group in the Side–Chain and their Complexes with $Cu^{2+}$ and $Ni^{2+}$" *Helvetica Chimica Acta*, 1986, 69, 2081–2086.

Gamana, et al., Bioconjugate Chem., 1990, 1, 319–324.

Letsinger, et al., "Cholesteryl–conjugated oligonucleotides: Synthesis, properties and activity as inhibitors of replication of human immunodeficiency virus in cell culture", *Proc. Natl. Acad. Sci. USA*, 1989, 86, 6553–6556.

Caruthers, "Synthesis of oligonucleotides and oligonucleotide analogues, Antisense inhibitors of gene expression", pp. 7–24, J.S. Cohen, ed., CRC Press, Boca Raton, FL, 1989.

Englisch, et al., "Chemically Modified Oligonucleotides as Probes and Inhibitors", *Angew. Chem. Int. Ed. Eng.*, 1991, 30, 613.

Goodchild, "Conjugates of Oligonucleotides and Modified Oligonucleotides: A Review of Their Synthesis and Properties", *Bioconjugate Chemistry*, 1990, 1, 165.

Manoharan, et al., "Chemical Modification to Improve Uptake and Bioavailability of Antisense Oligonucleotides", Database Embase Elsevier Science Publishers, 1992, 660, 306 (abstract).

Zon, G., "Oligonucleotide Analogues as Potential Chemotherapy Agents", *Pharmaceutical Research*, 1988, 5(9), 539–549.

Guschlbauer, W. And Jankowski, K., "Nucleoside conformation is Determined by the Electronegativity of the Sugar Substituent", *Nucleic Acids Research*, 1980, 8, 1421.

Ikehara, et al., "Recognition by Restriction Endonuclease EcoRI of Deoxyoctanucleotides Containing Modified Sugar Moieties", *Eur. J. Biochem.*, 1984, 139, 447–450.

Ikehara, et al., "A Linear Relationship Between Electronegativity of 2'–Substituents and Conformation of Adenine Nucleosides", *Tetrahedron Letters*, 1979, 42, 4073–4076.

Ikehara, et al., "Polynucleotides. LII.synthesis and properties of poly (2'–deox–2'–fluoroadenylic acid)", *Nucleic Acids Research*, 1978, 5, 1877–1887.

Ikehara, et al., "Polynucleotides. LVI. Synthesis and Properties of Poly(2'–deoxy–2'–fluoroinosinic Acid", *Nucleic Acids Research*, 1978, 5, 3315–3324.

Ikehara, et al., "Polynucleotides. L. Synthesis and properties of poly (2'chloro–2'–deoxyadenylic acid) and poly (2'–bromo–2'–deoxyadenylic acid", *Nucleic Acids Research*, 1977, 4, 4249–4260.

Eckstein, et al., "Polynucleotides Containing 2'–Chloro–2'–Deoxyribose", *Biochemistry*, 1972, 11, 4336–4344.

Inoue, et al., "Synthesis and hybridization studies on two complementary nona(2'–O–methyl) ribonucleotides", *Nucleic Acids Research*, 1987, 15, 6131–6148.

Shibahara, et al., "Inhibition of Human Immunodeficiency Virus (HIV–1) Replication by Synthetic Oligo–RNA Derivatives", *Nucleic Acids Research*, 1987, 17.

Stein, C.A. and Cohen, J.S., et al., "Oligodeoxynucleotides as Inhibitors of Gene Expression: A Review", *Cancer Research*, 1988, 48, 2659–2668.

Walder, J., "Antisense DNA and RNA: progress and prospects", *Genes & Development*, 1988, 2, 502–504.

Marcus–Sekura, C.J., et al., "Techniques for using antisense oligodeoxyribonucleotides to study gene expression", *Anal. Biochemistry*, 1988, 172, 289–295.

Zon, G., "Synthesis of backbone–modified DNA analogues for biological applications", *J. Protein Chem.*, 1987, 6, 131–145.

Zon, G., "Oligonucleotide analogues as potential chemotherapeutic agents", *Pharmaceutical Research*, 1988, 5, 539–549.

Van der Krol, et al., "Modulation of Aukaryotic Gene Expression by Complementary RNA or DNA Sequences", *BioTechniques*, 1988, 6, 958–973.

Loose–Mitchell, D.S., "Antisense Nucleic Acids as a Potential Class of Pharmaceutical Agents", *TIPS*, 1988, 9, 45–47.

Walder, R.Y. and Walder, J.A., "Role of RNase H in hybrid–arrested translation by antisense oligonucleotides", *Proc. Of Natl. Acad. Sci. USA*, 1988, 85, 5011–5015.

Stein, et al., "Physiochemical properties of Phosphorothioate Oligodeoxynucleotides and Experiments with 5'-Linked Intercalators", *Nucleic Acids Research*, 1988, 16, 3209–3221.

Agarwal, et al., "Synthesis and Enzymatic Properties of Deoxyribooligonucleotides Containing Methyl and Phenylphosphonate Linkages", *Nucleic Acids Research*, 1979, 6, 3009–3024.

Miller, et al., "Nonionic Nucleic Acid Analogues. Synthesis and characterization of dideoxyribonucleoside Methylphosphonates", *Biochemistry*, 1979, 18, 5134–5143.

Jayaraman, et al., "Selective inhibition of escherichia coli protein synthesis and growth by nonionic oligonucleotides complementary to the 3' end of 16S rRNA", *Proc. Natl. Acad. Sci. USA*, 1981, 78, 1537–1541.

Miller, et al., "Biochemical and Biological Effects of Nonionic Nucleic Acid Methylphosphonates", *Biochemistry*, 1981, 20, 1874–1880.

Miller, et al., "Synthesis and properties of adenine and thymine nucleoside alkyl phosphotriesters, the neutral analogs of dinucleoside monophosphates", *J. Am. Chem. Soc.*, 1971, 93. 6657–6665.

Agris, et al., "Inhibition of Vesicular Stomatitis Virus Protein Synthesis and Infection by Sequence–Specific Oligodeoxyribonucleoside Methylphosphonates", *Biochemistry*, 1986, 25, 6268–6275.

Smith, et al., "Antiviral effect of an oligo(nucleoside methylphosphonate) complementary to the splice junction of herpes simplex virus type I immediate early pre–mRNAs 4 and 5", *Proc. Natl. Acad. Sci. USA*, 1986, 83, 2787–2791.

Ruby, S.W. and Abelson, "An early hierarchic role of U1 small nuclear ribonucleoprotein in splicesome assembly", *Science*, 1988, 242, 1028–1035.

Tidd, et al., "Evaluation of N–ras oncogene anti–sense, sense and nonsense sequence methylphosphonate oligonucleotide analogues", *Anti–Cancer Drug Design*, 1988, 3, 117–127.

Roelen, et al., "Synthesis of nucleic acid methylphosphonothioates", *Nucleic Acid Research*, 1988, 16, 7633–7645.

Agarwal, et al., "Oligodeoxynucleoside Phosphoramidates and Phosphorothioates as Inhibitors of Human Immunodeficiency Virus", Proc. Natl. Acad. Sci. USA, 1988, 85, 7079–7083.

Matsukura, et al., "Phosphorothioate analogs of oligodeoxynucleotides: Inhibitors of replication and cytopathic effects of human immunodeficiency virus", *Proc. Natl. Acad. Sci. USA*, 1987, 84, 7706–7710.

Marcus–Sekura, et al., "Comparative inhibition of chloramphenicol acetyltransferase gene expression by antisense oligonucleotide anaogues having alkyl phosphotriester, methylphosphonate and phosphorothioate linkages", *Nucleic Acid Research*, 1987, 15, 5749–5763.

Brill, et al., "Synthesis of oligodeoxynucleoside phosphorodithioates via thioamidites", *J. Am. Chem. Soc.*, 1989, 111, 2321–2322.

Jager, et al., "Oligonucleotide N–alkylphosphoramidates; synthesis and binding to polynucleotides", *Biochemistry*, 1988, 27, 7237–7246.

Letsinger, et al., "Effects of pendant groups at phosphorus on binding properties of d–ApA analogues", *Nucleic Acids Research*, 1986, 14, 3487–3499.

Cazenave, et al., "Enzymatic amplification of translation inhibition of rabbitβ–globin mRNA mediated by anti–messenger oligodeoxynucleotides covalently linked to intercalating agents", *Nucleic Acid Research*, 1987, 15, 4717–4736.

Constant, et al., "Heterodimeric Molecules Including Nucleic Acid Bases and 9–Aminoacridine Spectroscopic Studies, Conformations, and Interactions with DNA", *Biochemistry*, 1988, 27, 3997–4003.

Yeung, et al., "Photoreactives and thermal properties of psoralen cross–links", *Biochemistry*, 1988, 27, 3204–3210.

Biggadike, et al., "Short convergent route to homochiral carbocyclic 2'–deoxynucleosides and carbocyclic robonucleosides", *J. Chem. Soc., Chem. Commun.*, 1987, 1083–1084.

Knorre, D.G. and Vlassov, V.V., "Complementary–addressed (sequence–specific) modification of nucleic acids", *Progress in Nucleic Acid Res. and Mol. Biol.*, 1985, 32, 291–320.

Le Doan, et al. "Sequence–Targeted Chemical Modifications of Nucleic Acids by Complementary Oligonucleotides Covalently Linked to Porphyrins", *Nucleic Acids Research*, 1987, 15, 8643–8659.

Sigman, D.S., "Nuclease Activity of 1,10–Phenanthroline–Copper Ion", *Accts. Chem. Res.*, 1986, 19, 180–186.

Dreyer, G.B. and Dervan, P.B., "Sequence–specific cleavage of single–stranded DNA Oligodeoxynucleotide–EDTA–Fe(II)", *Proc. Natl. Acad. Sci. USA*, 1985, 82, 968–972.

"The Chemistry of Heterocyclic Compounds", A. Weissberger, Ed., Imidazole and Derivatives, Part 1, Interscience, N.Y, 1953.

Outten, R.O. and Daves, G.D., Jr., "Synthetic 1–methoxybenzo[d]naphtho[1,2–b]pyran–6–one c–gylcosides", *J. Org. Chem.*, 1987, 52, 5064–5066.

Kazimierczuk, Z., et al., "Synthesis of 2'-deoxytubercidin, 2'–deoxyadenosine, and related 2'–deoxynucleosides via novel direct stereospecific sodium salt glycosylation procedure", *J. Am. Chem. Soc.*, 1984, 106, 6379–6382.

Revankar, et al., "Synthesis and Antiviral/Antitumor of Certain 3–Seazaguanine Nucleosides and Nucleotides", *J. Med. Chem.*, 1984, 27, 1389–1396.

Stufkens, et al., "Dynamic Jahn–Teller Effect in the Excited States of $SeCl_6^{2-}$, $SeBr_6^{2-}$, $TeCl_6^{2-}$ and $TeBr_6^{2-}$", *Rec. Trav. Chim.*, 1970, 89, 1185–1201.

Castle, R.N. and Seese, W.S., "Imidazo[4,5–D]pyridazines. I. Synthesis of 4,7–disubstituted derivatives", *J. Org. Chem.*, 1958, 23, 1534–1538.

Nucleic Acid Chemistry, Improved and New Synthetic Procedures, Methods and Techniques, Part 3, 1986, 229.

Suciu, et al., "Synthesis of 9–(2, 5–dideoxy–β–D–glycero–pent–4–enofuranosyl)adenine", *Carbohydr. Res.*, 1975, 44, 112–115.

Jones, R.A., in "Oligonucleotide Synthesis, A Practicle Approach", M.J. Gait, Ed., IRL Press, Washington, D.C. 1985.

Robins, et al., "Nucleic acid related compounds. 46. A general procedure for the efficient deoxygenation of secondary alcohols. regiospecific and stereoselective conversion of ribonucleosides to 2'–deoxynucleosides", *J. Am. Chem. Soc.*, 1983, 105, 4059–4065.

Jones, et al., "4'–substituted nucleosides. 5. Hydroxymethylation of nucleoside 5'–aldehydes", *J. Org. Chem.*, 1979, 44, 1309–1317.

Arnott, et al., "Optimised Parameters for A–DNA and B–DNA", *Biochem. & Biophys. Res. Commun.*, 1970, 47, 1504–1510.

Beaucage, et al., "Deoxynucleoside phosphoramidites—A new class of key intermediates for deoxypolynucleotide synthesis", *Tetrahedron Letters*, 1981, 22, 1859–1862.

Butke, et al., Nucleic Acid Chemistry, Part 3, pp. 149–152, Townsend and Tipson, eds., J. Wiley & Sons, N.Y., 1986.

Chen, Q.Y. and Wu, S.W., "Studies on Fluoroalkylation and Fluroalkoxylation. Part 33. Direct Trifluoromethylation of Aryl Halides with Fluorosulphonyldifluoromethyl Iodide in the Presence of Copper: an Electron Transfer Induced Process", *J. Chem. Soc. Perkin Trans.*, 1989, 2385–2387.

Chladek, et al., J. Carbohyd., Nucleotides & Nucleosides, 1980, 7, 63–75.

Ikehara, M. and Miki, H., "Studies of Nucleosides and Nucleotides–LXXXII.[1)] cyclonucleosides (39).[2)]synthesis and properties of 2'halogen–2'–deoxyadenosines", *Chem. and Pharm. Bull.*, 1978, 26, 2449–2453.

Ikehara, M., "Studies of Nucleosides and Nucleotides–LXXIX.[1)], Purine Cyclonucleosides. (37). The total synthesis of an antibiotic 2'–amino–2'deoxyguanosine[2)]", *Chem. and Pharm. Bull.*, 1978, 26, 240–244.

De las Heras, et al., "3'–C–Cyano–3'–Deoxythymidine", *Tetrahedron Letters*, 1988, 29, 941–944.

Codington, et al., "Nucleosides. XVIII. Synthesis of 2'–Flurorothymidine, 2'–Fluorodeoxyuridine, and Other 2'–Halogeno–2'–Deoxy Nucleosides", *J. Org. Chem.*, 1964, 29, 558–564.

Freskos, "Synthesis of 2'Deoxypyrimidine Nucleosides Via Copper (I) Iodide Catalysis", Nucleosides & Nucleotides, 1989, 8, 1075–1076.

Gait, ed., Oligonucleotide Synthesis, A Practical Approach, IRL Press, Washington, D.C., 1984.

Hertel, et al. "Synthesis of 2–deoxy–2,2–difluoro–D–ribose and 2–deoxy–2,2–difluoro–D–ribofuranosyl nucleosides", *J. Org. Chem.*, 1988, 53, 2406–2409.

Ikehara, et al., "Studies of Nucleosides and Nucleotides–LXXIV.[1)] Purine Cyclonucleosides—34 A New Method for the Synthesis of 2'–substituted 2'–deoxyadenosines", *Tetrahedron*, 1978, 34, 1133–1138.

Ikehara, et al., "Studies of Nucleosides and Nucleotides–LXV[1] Purine cyclonuceosides–26 A Versatile Method for the Synthesis of Purine O–cyclo–Nucleosides. The First Synthesis of 8,2'–Anhydro–8–Oxy 9–β–D–Arabinofuranosylguanine", *Tetrahedron*, 1975, 31, 1369–1372.

Ikehara, et al., "Purine 8–cyclonucleosides", *Accts. Chem. Res.*,1969, 2, 47–53.

Ikehara, et al., "Improved Synthesis of 2'–fluoro–2'–deoxyadenosine and synthesis and Carbon–13 NMR Spectrum of its 3',5'–cyclic Phosphate Derivative", *Nucleosides & Nucleotides*, 1983, 2, 373–385.

Ikehara, M. And Imura, J., "Studies of Nucleosides and Nucleotides–LXXXV11.[1)], Purine cyclonucleosides. XII. Synthesis of 2'deoxy–2' fluorofunaosine", *Chem. & Pharm. Bull.*, 1981, 29, 1034–1038.

Ikehara, M. And Imura, J., "Studies of Nucleosides and Nucleotides–LXXXIV., Purine cclonuceosides. (43). Synthesis and properties of 2'halogen–2'–deoxyguanosines[1)]", *Chem. & Pharm. Bull.*, 1981, 29, 3281–3285.

Jarvi, et al., "Synthesis and biological evaluation of dideoxunucleosides containing a difluromethylene unit", *Nucleosides & Nucleotides*, 1989, 8, 1111–1114.

Jones, et al., "Transient protection: Efficient one–flask synthesis of protected deoxynuceosides", *J. Am. Chem. Soc.*, 1982, 104, 1316–1319.

Koole, et al., "Synthesis of phosphate–methylated DNA fragments using 9–fluorenylmethoxycarbonyl as transient base protecting group", *J. Org. Chem.*, 1989, 54, 1657–1664.

Markiewicz, W.T. and Wiewiorowski, M., in Nucleic Acid Chemistry, Part 3, pp. 222–231, Townsend and Tipson, eds., John Wiley & Sons, New York, 1986.

Damha, et al., "Solution and solid phase chemical synthesis of arabinonucleotides", *Can. J. Chem.*, 1989. 67, 831–839.

Parkes, K.E.B. and Taylor, K., "A short synthesis of 3'–cyano–3'–Deoxythymidine", *Tetrahedron Letters*, 1988, 29, 2995–2996.

Ranganathan, R., "Modification of the $2^1$–Position of Purine Nucleosides: Synthesis of $2^1$–a–Substituted–$2^1$–Deoxyadenosine Analogs", *Tetrahedron Letters*, 1977, 15, 1291–1294.

Sproat, et al., "Highly Efficient Chemical Synthesis of 2'–O–methylioligoribunocleotides and Tetrabiotinylated Derivatives; Novel Probes That are Resistant to Degradtion by RNA or DNA Specific Nucleases", *Nucleic Acids Research*, 1989, 17, 3373–3386.

Sproat, et al., "New synthetic routes to protected purine 2'–O–methylriboside –3'–O–phosphoramidites using a novel alkylation procedure", *Nucleic Acids Research*, 1990, 18, 41–49.

B.G. DeLa Torre et al. Nucleosides and Nucleotides, vol. 12, No. 9, pp. 993–1005 (1993).*

J.T. Goodwin et al. Tetrahedron Letters. vol. 34. No. 35, pp. 5549–5552 1993.*

J.P. Collman et al. J. of the American Chemical Society. vol. 104. No. 5 pp. 1391–1403 1982.*

B.A. Connelly. Nucleic Acid Research. vol. 13. No. 12 pp. 4485–4502 1985.*

W. Bannwarth et al. Helvetica Ghimica Acta. vol. 73 pp. 1139–1147 1990.*

M. Manoharan et al. Gene. vol. 149. pp. 147–156 1994.*

M. Manoharan et al. Bioorganic And Medicinal Chemistry Letters. vol. 3. No. 12 pp. 2765–2770 1993.*

\* cited by examiner

SEQUENCE LISTING

```
(1) GENERAL INFORMATION:

(iii) NUMBER OF SEQUENCES: 5

(2) INFORMATION FOR SEQ ID NO:1:

(i) SEQUENCE CHARACTERISTICS:
        (A) LENGTH: 5 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: misc_feature
        (B) LOCATION: 3
        (D) OTHER INFORMATION: /note=
            "2'-O-thiol modified-2'-deoxyadenosine"

(xi) SEQUENCE DESCRIPTION: SEQ ID NO:1:

GAACT                                                           5

(2) INFORMATION FOR SEQ ID NO:2:

(i) SEQUENCE CHARACTERISTICS:
        (A) LENGTH: 5 base pairs
        (B) TYPE: nucleic acid
```

```
        (C) STRANDEDNESS: single
        (D) TOPOLOGY: linear (ii) MOLECULE TYPE: DNA (genomic)

(ix) FEATURE:
        (A) NAME/KEY: misc_feature
        (B) LOCATION: 3
        (D) OTHER INFORMATION: /note=
            "2'-O-thiol modified-2'-deoxyadenosine"

(xi) SEQUENCE DESCRIPTION: SEQ ID NO:2:

GAACT                                                                   5

(2) INFORMATION FOR SEQ ID NO:3:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: misc_feature
        (B) LOCATION: 5
        (D) OTHER INFORMATION: /note=
            "2'-O-thiol modified-2'-deoxyadenosine"

(xi) SEQUENCE DESCRIPTION: SEQ ID NO:3:

TGGGAGCCAT AGCGAGCC                                                    18

(2) INFORMATION FOR SEQ ID NO:4:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: misc_feature
        (B) LOCATION: 20
        (D) OTHER INFORMATION: /note=
            "2'-O-thiol modified-2'-deoxyadenosine"

(xi) SEQUENCE DESCRIPTION: SEQ ID NO:4:

TCTGAGTAGC AGAGGAGCTA AG                                               22

(2) INFORMATION FOR SEQ ID NO:5:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: misc_feature
        (B) LOCATION: 1
        (D) OTHER INFORMATION: /note=
            "2'-O-thiol modified-2'-deoxyadenosine"

(ix) FEATURE:
        (A) NAME/KEY: misc_feature
        (B) LOCATION: 15
        (D) OTHER INFORMATION: /note=
            "2'-O-thiol modified-2'-deoxyadenosine"
```

(xi) SEQUENCE DESCRIPTION: SEQ ID NO:5:

ATCGGCTTTT GCCGAT                                                              16

THIOL-DERIVATIZED NUCLEOSIDES AND OLIGONUCLEOSIDES

CROSS REFERENCE TO RELATED APPLICATIONS

This patent application is continuation of application Ser. No. 08/924,326, filed on Sep. 5, 1997, now U.S. Pat. No. 6,114,513, which is a continuation of application Ser. No. 08/458,396, filed on Jun. 2, 1995 (now U.S. Pat. No. 5,852,182), which is a continuation-in-part of application Ser. No. 08/116,801, filed Sep. 3, 1993 (now U.S. Pat. No. 5,578,718), which is a 371 PCT/US92/09196, filed Oct. 23, 1992 (now Ser. No. 08/211,882, filed Apr. 22, 1994now U.S. Pat. No. 6,153,737), which is a continuation-in-part of application Ser. No. 07/782,374, filed Oct. 24, 1991 (now abandoned), which is a continuation-in-part of application Ser. No. 07/463,358, filed Jan. 11, 1990 (now abandoned), and of application Ser. No. 07/566,977, filed Aug. 13, 1990 (now abandoned).

FIELD OF THE INVENTION

This application is directed to nucleosides, oligonucleotides and oligonucleosides functionalized to include alkylthiol chemical functionalities, and derivatives thereof. In certain embodiments, the compounds of the invention further include steroids, reporter molecules, reporter enzymes, lipophilic molecules, peptides or proteins attached to the nucleosides, oligonucleotides or oligonucleosides through the alkylthio group.

BACKGROUND OF THE INVENTION

Messenger RNA (mRNA) directs protein synthesis. Antisense methodology is the complementary hybridization of relatively short oligonucleotides to mRNA or DNA such that the normal, essential functions of these intracellular nucleic acids are disrupted. Hybridization is the sequence-specific hydrogen bonding via Watson-Crick base pairs of oligonucleotides to RNA or single-stranded DNA. Such base pairs are said to be complementary to one another.

The naturally occurring events that provide the disruption of the nucleic acid function, discussed by Cohen in *Oligonucleotides: Antisense Inhibitors of Gene Expression*, CRC Press, Inc., Boca Raton, Fla. (1989) are thought to be of two types. The first, hybridization arrest, denotes the terminating event in which the oligonucleotide inhibitor binds to the target nucleic acid and thus prevents, by simple steric hindrance, the binding of essential proteins, most often ribosomes, to the nucleic acid. Methyl phosphonate oligonucleotides (Miller, et al., *Anti-Cancer Drug Design* 1987, 2, 117) and α-anomer oligonucleotides are the two most extensively studied antisense agents which are thought to disrupt nucleic acid function by hybridization arrest.

The second type of terminating event for antisense oligonucleotides involves the enzymatic cleavage of the targeted RNA by intracellular RNase H. A 2'-deoxyribofuranosyl oligonucleotide or oligonucleotide analog hybridizes with the targeted RNA and this duplex activates the RNase H enzyme to cleave the RNA strand, thus destroying the normal function of the RNA. Phosphorothioate oligonucleotides are the most prominent example of an antisense agent that operates by this type of antisense terminating event.

Considerable research is being directed to the application of oligonucleotides and oligonucleotide analogs as antisense agents for diagnostics, research reagents and potential therapeutic purposes. At least for therapeutic purposes, the antisense oligonucleotides and oligonucleotide analogs must be transported across cell membranes or taken up by cells to express activity. One method for increasing membrane or cellular transport is by the attachment of a pendant lipophilic group.

Ramirez, et al., *J. Am. Chem. Soc.* 1982, 104, 5483, introduced the phospholipid group 5'-O-(1,2-di-O-myristoyl-sn-glycero-3-phosphoryl) into the dimer TpT independently at the 3' and 5' positions. Subsequently Shea, et al., *Nuc. Acids Res.* 1990, 18, 3777, disclosed oligonucleotides having a 1,2-di-O-hexyldecyl-rac-glycerol group linked to a 5'-phosphate on the 5'-terminus of the oligonucleotide. Certain of the Shea, et. al. authors also disclosed these and other compounds in patent application PCT/US90/01002. A further glucosyl phospholipid was disclosed by Guerra, et al., *Tetrahedron Letters* 1987, 28, 3581.

In other work, a cholesteryl group was attached to the inter-nucleotide linkage between the first and second nucleotides (from the 3' terminus) of an oligonucleotide. This work is disclosed in U.S. Pat. No. 4,958,013 and further by Letsinger, et al., *Proc. Natl. Acad. Sci. USA* 1989, 86, 6553. The aromatic intercalating agent anthraquinone was attached to the 2' position of a sugar fragment of an oligonucleotide as reported by Yamana, et al., *Bioconjugate Chem.* 1990, 1, 319.

Lemairte, et al., *Proc. Natl. Acad. Sci. USA* 1986, 84, 648; and Leonetti, et al., *Bioconjugate Chem.* 1990, 1, 149. The 3' terminus of the oligonucleotides each include a 3'-terminal ribose sugar moiety. The poly(L-lysine) was linked to the oligonucleotide via periodate oxidation of this terminal ribose followed by reduction and coupling through a N-morpholine ring. Oligonucleotide-poly(L-lysine) conjugates are described in European Patent application 87109348.0. In this instance the lysine residue was coupled to a 5' or 3' phosphate of the 5' or 3' terminal nucleotide of the oligonucleotide. A disulfide linkage has also been utilized at the 3' terminus of an oligonucleotide to link a peptide to the oligonucleotide as is described by Corey, et al., *Science* 1987, 238, 1401;

Zuckermann, et al., *J. Am. Chem. Soc.* 1988, 110, 1614; and Corey, et al., *J. Am. Chem. Soc.* 1989, 111, 8524.

Nelson, et al., *Nuc. Acids Res.* 1989, 17, 7187 describe a linking reagent for attaching biotin to the 3'-terminus of an oligonucleotide. This reagent, N-Fmoc-O-DMT-3-amino-1, 2-propanediol is now commercially available from Clontech Laboratories (Palo Alto, Calif.) under the name 3'-Amine on. It is also commercially available under the name 3'-Amino-Modifier reagent from Glen Research Corporation (Sterling, Va.). This reagent was also utilized to link a peptide to an oligonucleotide as reported by Judy, et al., *Tetrahedron Letters* 1991, 32, 879. A similar commercial reagent (actually a series of such linkers having various lengths of polymethylene connectors) for linking to the 5'-terminus of an oligonucleotide is 5'-Amino-Modifier C6. These reagents are available from Glen Research Corporation (Sterling, Va.). These compounds or similar ones were utilized by Krieg, et al., *Antisense Research and Development* 1991, 1, 161 to link fluorescein to the 5'-terminus of an oligonucleotide. Other compounds of interest have also been linked to the 3'-terminus of an oligonucleotide. Asseline, et al., *Proc. Natl. Acad. Sci. USA* 1984, 81, 3297 described linking acridine on the 3'-terminal phosphate group of an poly (Tp) oligonucleotide via a polymethylene linkage. Haralambidis, et al., *Tetrahedron Letters* 1987, 28, 5199 report building a peptide on a solid state support and then linking an oligonucleotide to that peptide via the 3' hydroxyl group of the 3' terminal nucleotide of the oligonucleotide. Chollet, *Nucleosides & Nucleotides* 1990, 9, 957 attached an Aminolink 2 (Applied Biosystems, Foster City, Calif.) to the 5' terminal phosphate of an oligonucleotide. They then used the bifunctional linking group SMPB (Pierce Chemical Co., Rockford, Ill.) to link an interleukin protein to the oligonucleotide.

An EDTA iron complex has been linked to the 5 position of a pyrimidine nucleoside as reported by Dreyer, et al., *Proc. Natl. Acad. Sci. USA* 1985, 82, 968. Fluorescein has been linked to an oligonucleotide in the same manner as reported by Haralambidis, et al., *Nucleic Acid Research* 1987, 15, 4857 and biotin in the same manner as described in PCT application PCT/US/02198. Fluorescein, biotin and pyrene were also linked in the same manner as reported by Telser, et al., *J. Am. Chem. Soc.* 1989, 111, 6966. A commercial reagent, Amino-Modifier-dT, from Glen Research Corporation (Sterling, Va.) can be utilized to introduce pyrimidine nucleotides bearing similar linking groups into oligonucleotides.

Sproat, et al., *Nucl. Acids Res.* 1987, 15, 4837, have synthesized 5'-mercapto nucleosides and incorporated them into oligonucleotides. Several phosphoramidites and H-phosphonates have been reported for introduction of a 5'-thiol linker via a phosphate linkage (see, Mori, et. al., *Nucleosides and Nucleotides*, 1989, 8, 649; WO 89/02931 (Levenson, et al.) published Apr. 6, 1989; Sinha, et al., *Nucl. Acids. Res.* 1988, 16, 2659). The amidites provide means for attachment of a HS—$(CH_2)_n$—O—P(=O)—O—linkage to the oligomer. Also, disulfide-protected mercapto alkanols have been used to yield phosphoramidites (available from Glen Research, Sterling, Va. and Clontech, Palo Alto, Calif.). The same mercapto alkanoles have been attached to controlled pore glass (CPG) to give solid supports which yield 3'-thiolated oligonucleotides having a phosphate or thiophosphate linkage between the linker and the oligonucleotide. In another approach, oligonucleotides having 5'-amino linkers have been converted into oligonucleotides having 5'-thiol linkers by treatment with dithiobis-(N-succinimidyl) propionate or N-succinimidyl-3-(2-pyridyldithio) propionate followed by dithiothreitol (DTT) (See, Bischoff, et al., *Anal. Biochem.* 1987, 164, 336 and Gaur, et al., *Nucl. Acids Res.* 1989, 17, 4404). Asseline, et al., *Tetrahedron* 1992, 48, 1233 and Fidanza, et al., *J. Am. Chem. Soc.* 1992, 114, 5509, have used either the terminal or internucleotide thiosphophate groups to attach pendant groups. Fidanza, et al., *J. Org. Chem.* 1992, 57, 2340, have used cystamine ($H_2N$—$CH_2$—$CH_2$—S—S—$CH_2$—$CH_2$—$NH_2$) to oxidize internucleotide H-phosphonate and provide a —P—NH—$CH_2$—$CH_2$—SH tether. Zuckerman, et. al., *Nucleic Acids Res.* 1987, 15, 5305, have used a 3'-S-alkyl thiol linker in a thymine nucleoside and incorporated the nucleoside into oligonucleotides. Ferentz, et al., (*J. Org. Chem.* 1990, 55, 5931 and *J. Am. Chem. Soc.* 1991, 113, 4000) have shown methods of attaching —NH—$(CH_2)_n$—SH (n=2,3) at the 4-position of cytosine and the 6-position of adenosine.

However, there still remains a need in the art for methods of synthesis for nucleosides and oligonucleosides bearing further thiol-containing species.

OBJECTS OF THE INVENTION

It is one object of this invention to provide nucleosides, oligonucleotides and oligonucleosides that include alkylthiol chemical functionality.

It is a further object of the invention to provide compounds having improved transfer across cellular membranes.

It is another object to provide compounds that include intercalators, nucleic acid cleaving agents, cell surface phospholipids, and/or diagnostic agents.

It is yet another object to provide improvements in research and diagnostic methods and materials for assaying bodily states in animals, especially disease states.

It is an additional object of this invention to provide therapeutic and research materials having improved transfer and up take properties for the treatment of diseases through modulation of the activity of DNA or RNA.

BRIEF DESCRIPTION OF THE INVENTION

These and other objects are satisfied by the present invention, which provides compounds containing alkylthiol chemical functionality. In one aspect, the invention provides nucleosides having base portions and ribofuranosyl sugar portions. Such nucleosides bear at a 2'-O-position, a 3'-O-position, or a 5'-O-position a substituent having formula:

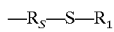

where:

$R_S$ has formula $R_A$, $R_A$—C(O)—Q—$R_A$, $R_A$—Q—$R_A$—Q—$R_A$;

each $R_A$ is independently selected from alkyl having 1 to about 10 carbon atoms;

each Q is independently selected from NH, O, and S;

$R_1$ is H or a thiol protecting group or has formula S—$R_2$, $CH_2C(O)$—NH—$R_2$, $CH_2$—CH=CH—C(O)—$R_2$, —$CH_2$—$CH_2$—NH—$S(O)_2$—$R_2$, or (maleimido)-$R_2$; and $R_2$ includes a steroid molecule, a reporter molecule, a lipophilic molecule, a reporter enzyme, a peptide, a protein, a reporter group, an alkylator, an intercalator, a cell receptor binding molecule, a crown ether, a crown amine, a porphyrin, a crosslinking agent, a peptide nucleic acid, or a thiol attached to a poly (ethylene glycol).

In another aspect, the invention provides oligonucleotides and oligonucleosides each comprising a plurality of linked nucleosides, wherein each nucleoside includes a ribofuranosyl sugar portion and a base portion and at least one (preferably more than one) of the nucleosides bears at a 2'-O-position, a 3'-O-position, or a 5'-O-position a substituent having formula —$R_A$—S—$R_1$.

In yet another aspect, the invention provides nucleosides that bear at a 5-pyrimidine position or at a 2-, 6-, or 8-purine position a substituent having formula —Q—$R_A$—S—$R_1$, —C≡C—$R_A$—Q—C(O)—$R_A$—S—$R_1$, —CH=CH—C(O)—Q—$R_A$—S—$R_1$, or —CH=CH—$R_A$—Q—C(O)—Q—$R_A$—S—$R_1$, provided that a 6-purine substituent does not have formula —NH—$R_A$—S—$R_1$ when $R_1$ is H or a thiol protecting group. Also provided are oligonucleosides or oligonucleotides containing one or more of such nucleosides.

The invention also provides oligonucleotides comprising at least two nucleosides bound by a linkage having formula (5')-O—P[X][Q—$R_A$—S—$R_1$]—O-(3') wherein X is O or S, provided that Q is not NH when $R_1$ is H or a thiol protecting group.

In another aspect the invention provides methods for preparing oligonucleotides and oligonucleosides comprising the steps of contacting nucleosides according to the invention for a time and under reaction conditions effective to form a covalent bond therebetween. In preferred embodiments, at least one of the nucleosides bears a phosphoramidate group at its 2'-O-position or at its 3'-O-position.

In other embodiments, compounds according to the invention are prepared by contacting a nucleoside, oligonucleotide or oligonucleoside with derivatizing reagents. For example, a nucleoside, oligonucleotide or oligonucleoside bearing a 2'-hydroxy group, a 3'-hydroxy group, or a 5'-hydroxy group under basic conditions with a compound having formula $L_1$—$R_A$—S—$R_{1a}$ wherein $L_1$ is a leaving group such as a halogen and $R_{1a}$ is a thiol protecting group.

The present invention also provides methods for inhibiting the expression of particular genes in the cells of an organism, comprising administering to said organism a compound according to the invention. Also provided are methods for inhibiting transcription and/or replication of particular genes or for inducing degradation of particular regions of double stranded DNA in cells of an organism by administering to said organism a compound of the invention. Further provided are methods for killing cells or virus by contacting said cells or virus with a compound of the invention. The compound can be included in a composition that further includes an inert carrier for the compound.

DETAILED DESCRIPTION OF THE INVENTION

This invention provides nucleosides, oligonucleotides and oligonucleosides containing alkylthiol chemical functionality. The nucleoside subunits can be "natural" or "synthetic" moieties. Each nucleoside is formed from a naturally occurring or synthetic base and a naturally occurring or synthetic pentofuranosyl sugar group.

The term "oligonucleotide" refers to a polynucleotide formed from a plurality of linked nucleotide units. The nucleotide units each include a nucleoside unit. In the context of this invention, the term "oligonucleoside" refers to a plurality of nucleoside units that are linked together. In a generic sense, since each nucleotide unit of an oligonucleotide includes a nucleoside therein, the term "oligonucleoside" can be considered to be inclusive of oligonucleotides (i.e., nucleosides linked together via phosphate linking groups). In a further sense, the term "oligonucleoside" also refers to a plurality of nucleosides that are linked together via linkages other than phosphate linkages. The term "oligonucleoside" thus effectively includes naturally occurring species or synthetic species formed from naturally occurring subunits. For brevity, the term "oligonucleoside" will be used to denote both phosphate linked (oligonucleotides) and non-phosphate linked polynucleoside species.

Oligonucleosides according to the invention also can include modified subunits. Representative modifications include modification of a heterocyclic base portion of a nucleoside or a sugar portion of a nucleoside. Exemplary modifications are disclosed in the following U.S. patent applications: Ser. No. 07/463,358, filed Jan. 11, 1990, now abandoned, entitled Compositions And Methods For Detecting And Modulating RNA Activity; Ser. No. 07/566,977, filed Aug. 13, 1990, now abandoned, entitled Sugar Modified oligonucleotides That Detect And Modulate Gene Expression; Ser. No. 07/558,663, filed Jul. 27, 1990, now U.S. Pat. No. 5,138,045, entitled Novel Polyamine Conjugated Oligonucleotides; Ser. No. 07/558,806, filed Jul. 27, 1991, now abandoned, entitled Nuclease Resistant Pyrimidine Modified Oligonucleotides That Detect And Modulate Gene Expression and Ser. No. PCT/US91/00243, filed Jan. 11, 1991, entitled Compositions and Methods For Detecting And Modulating RNA Activity. Each of these patent applications are assigned to the assignee of this invention. The disclosure of each is incorporated herein by reference.

The term oligonucleoside thus refers to structures that include modified portions, be they modified sugar moieties or modified base moieties, that function similarly to natural bases and natural sugars. Representative modified bases include deaza or aza purines and pyrimidines used in place of natural purine and pyrimidine bases; pyrimidines having substituent groups at the 5 or 6 position; and purines having altered or replacement substituent groups at the 2, 6 or 8 positions. Representative modified sugars include carbocyclic or acyclic sugars, sugars having substituent groups at their 2' position, and sugars having substituents in place of one or more hydrogen atoms of the sugar. Other altered base moieties and altered sugar moieties are disclosed in U.S. Pat. No. 3,687,808 and PCT application PCT/US89/02323.

Altered base moieties or altered sugar moieties also include other modifications consistent with the spirit of this invention. Such oligonucleosides are best described as being structurally distinguishable from yet functionally interchangeable with naturally occurring or synthetic wild type oligonucleotides. All such oligonucleosides are comprehended by this invention so long as they function effectively to mimic the structure of a desired RNA or DNA strand.

For use in antisense methodology, the oligonucleosides of the invention preferably comprise from about 10 to about 30 subunits. It is more preferred that such oligonucleosides comprise from about 15 to about 25 subunits. As will be appreciated, a subunit is a base and sugar combination suitably bound to adjacent subunits through, for example, a phosphorous-containing (e.g., phosphodiester) linkage or some other linking moiety. The nucleosides need not be linked in any particular manner, so long as they are covalently bound. Exemplary linkages are those between the 3'- and 5'-positions or 2'- and 5'-positions of adjacent nucleosides. Exemplary linking moieties are disclosed in the following references: Beaucage, et al., *Tetrahedron* 1992, 48, 2223 and references cited therein; and U.S. patent applications: Ser. No. 07/703,619, filed May 21, 1991; Ser. No. 07/903,160, filed Jun. 24, 1992; Ser. No. 08/039,979, filed Mar. 20, 1993; Ser. No. 08/039,846, filed Mar. 30, 1993; and Ser. No. 08/040,933, filed Mar. 31, 1993. Each of the foregoing patent applications are assigned to the assignee of this invention. The disclosure of each is incorporated herein by reference.

It is preferred that the RNA or DNA portion which is to be modulated using oligonucleosides of the invention be preselected to comprise that portion of DNA or RNA which codes for the protein whose formation or activity is to be modulated. The targeting portion of the composition to be employed is, thus, selected to be complementary to the preselected portion of DNA or RNA, that is, to be an antisense oligonucleoside for that portion. Preferred embodiments of this invention include those the compounds of the invention that are complementary to sequences for herpes, papilloma and other viruses.

The nucleosides and oligonucleosides of the invention can be used in diagnostics, therapeutics and as research reagents and kits. They can be used in pharmaceutical compositions by including a suitable pharmaceutically acceptable diluent or carrier. They further can be used for treating organisms having a disease characterized by the undesired production of a protein. The organism should be contacted with an oligonucleotide having a sequence that is capable of specifically hybridizing with a strand of nucleic acid coding for the undesirable protein. Treatments of this type can be practiced on a variety of organisms ranging from unicellular prokaryotic and eukaryotic organisms to multicellular eukaryotic organisms. Any organism that utilizes DNA-RNA transcription or RNA-protein translation as a fundamental part of its hereditary, metabolic or cellular control is susceptible to therapeutic and/or prophylactic treatment in accordance with the invention. Seemingly diverse organisms such as bacteria, yeast, protozoa, algae, all plants and all higher animal forms, including warm-blooded animals, can be treated. Further, each cell of multicellular eukaryotes can be treated since they include both DNA-RNA transcription and RNA-protein translation as integral parts of their cellular activity. Many of the organelles (e.g., mitochondria and chloroplasts) of eukaryotic cells also include transcription and translation mechanisms. Thus, single cells, cellular populations or organelles can also be included within the definition of organisms that can be treated with therapeutic or diagnostic oligonucleotides. As used herein, therapeutics is meant to include the eradication of a disease state, by killing an organism or by control of erratic or harmful cellular growth or expression.

In one aspect, the present invention is directed to nucleosides and oligonucleosides that bear at least one thiol-containing substituent at a ribofuranosyl, pyrimidinyl, and/or purinyl position. Ribofuranosyl substituents preferably have formula —$R_A$—S—$R_1$ and are appended at 2'-O-, 3'-O-, and/or 5'-O-positions. Pyrimidinyl and purinyl substituents preferably have formula —C≡C—$R_A$—Q—C(O)—$R_A$—S—$R_1$ and are appended at 5-pyrimidine positions and at 2-, 6-, or 8-purine positions.

In another aspect, the invention is directed to oligonucleosides containing at least one internucleoside linkage having formula (5')-O—P[X][Q—$R_A$—S—$R_1$]—O-(3').

Each $R_A$ according to the invention is an alkyl moiety independently selected to having 1 to about 10 carbon atoms. The term "alkyl" is intended to include straight chain and branched hydrocarbons. Preferred $R_A$ have 1 to about 7 carbon atoms, more preferably 2 to about 6 carbon atoms. $R_A$ having formula $(CH)_n$ where n=1–10 are preferred.

$R_1$ according to the invention is H, a thiol protecting group (preferably an acid labile protecting group) or has formula S—$R_2$, $CH_2C(O)$—NH—$R_2$, $CH_2$—CH=CH—C(O)—$R_2$, —$CH_2$—$CH_2$—NH—$S(O)_2$—$R_2$, or (maleimido)-$R_2$. Numerous thiol protecting groups are known in the art, including, but not limited to, the triphenylmethyl (trityl; Tr) and S-t-butyl, S-p-nitrobenzyl, and S-p-methoxy-benzyl (see, e.g., Greene and Wuts, Protective Groups in Organic Synthesis, 2d edition, John Wiley & Sons, New York, 1991). Preferred maleimido moieties are those that are N-substituted with $R_2$ and 3-substituted with S.

$R_2$ can include a steroid molecule, a reporter molecule, a lipophilic molecule, a reporter enzyme, a peptide, a protein, a reporter groups, an alkylator, an intercalator, a cell receptor binding molecule, a crown amine (a "cyclam"), a porphyrin, a crosslinking agent, a peptide nucleic acid, or a thiol attached to a poly(ethyleneglycol) (PEG; —$(CH_2CH_2O)_{1-200}$) group. That is, $R_2$ can include a substituent consisting essentially of the foregoing groups.

For the purposes of this invention the terms "reporter molecule" and "reporter enzyme" are inclusive of those molecules or enzymes that have physical or chemical properties that allow them to be identified in gels, fluids, whole cellular systems, broken cellular systems and the like utilizing physical properties such as spectroscopy, radioactivity, calorimetric assays, fluorescence, and specific binding. Particularly useful as reporter molecules are biotin and fluorescein dyes. Particularly useful as reporter enzymes are alkaline phosphatase and horseradish peroxidase.

Steroids include those chemical compounds that contain a perhydro-1,2-cyclopentanophenanthrene ring system. Particularly useful as steroid molecules are the bile acids including cholic acid, deoxycholic acid and dehydrocholic acid; steroids including cortisone, digoxigenin, testosterone and cholesterol and even cationic steroids such as cortisone having a trimethylaminomethyl hydrazide group attached via a double bond at the 3 position of the cortisone rings.

Proteins and peptides are utilized in their usual sense as polymers of amino acids. Normally peptides comprise such polymers that contain a smaller number of amino acids per unit molecule than do the proteins. Particularly useful as peptides and proteins are sequence-specific peptides and proteins including phosphodiesterase, peroxidase, phosphatase and nuclease proteins. Such peptides and proteins include SV40 peptide, RNaseA, RNase H and Staphylococcal nuclease.

Lipophilic molecules include naturally-occurring and synthetic aromatic and non-aromatic moieties such as fatty acids, esters, alcohols and other lipid molecules, cage structures such as adamantane and buckminsterfullerenes, and aromatic hydrocarbons such as benzene, perylene, phenanthrene, anthracene, naphthalene, pyrene, chrysene, and naphthacene. Particularly useful as lipophilic molecules are alicyclic hydrocarbons, saturated and unsaturated fatty acids, waxes, terpenes and polyalicyclic hydrocarbons including adamantane and buckminsterfullerenes. Particularly useful as terpenoids are vitamin A, retinoic acid, retinal and dehydroretinol.

Alkylators according to the invention are moieties that can effect attachment of electrophilic groups to targeted molecular structures. Representative alkylators are disclosed by Meyer, et al., *J. Am. Chem. Soc.* 1989, 111, 8517.

Intercalators are polycyclic aromatic moieties that can insert between adjacent base pairs without affecting normal Watson-Crick base pairing. Representative intercalators are disclosed by Manoharan in Antisense Research and Applications, Crooke and Lebleu, eds., CRC Press, Boca Raton, 1993.

Cell receptor binding molecules according to the invention are vitamins and carbohydrate moieties for which specific receptors exist within a cell. Representative cell receptor binding molecules are disclosed by Application Serial No. PCT/US92/09196, filed Oct. 23, 1992, the contents of which are incorporated herein by reference.

Crosslinking agents are moieties that can effect intrastrand or interstrand covalent binding of RNA and/or DNA. Representative crosslinking agents are disclosed in International Patent Application Serial No. PCT/US93/02059, filed Mar. 5, 1993, which is incorporated herein by reference. Useful crown amines are disclosed by Studer, et al., Helv. Chim. Acta 1986, 69, 2081 and Smith-Jones, et al., *Bioconjugate Chem.* 1991, 2, 415. Peptide nucleic acids are disclosed by International Patent Application WO 92/20702, published Nov. 26, 1992.

Oligonucleosides according to the invention can be assembled in solution or through solid-phase reactions, for example, on a suitable DNA synthesizer utilizing nucleosides according to the invention and/or standard nucleotide precursors. The nucleosides and nucleotide precursors can already bear alkylthio groups or can be later modified to bear such groups.

In the former case, compounds according to the invention are prepared by, for example, reacting nucleosides bearing at least one free 2'-, 3'-, or 5'-hydroxyl group under basic conditions with a compound having formula $L_1$—$(CH_2)_n$—S—$R_{1a}$ where $L_1$ is a leaving group and $R_{1a}$ is a thiol protecting group. Displacement of the leaving group through nucleophilic attack of an oxygen anion produces the desired thiol derivative. Leaving groups according to the invention include but are not limited to halogen, alkylsulfonyl, substituted alkylsulfonyl, arylsulfonyl, substituted arylsulfonyl, hetercyclcosulfonyl or trichloroacetimidate. A more preferred group includes chloro, fluoro, bromo, iodo, p-(2,4-dinitroanilino)benzenesulfonyl, benzenesulfonyl, methylsulfonyl (mesylate), p-methylbenzenesulfonyl (tosylate), p-bromobenzenesulfonyl, trifluoromethylsulfonyl (triflate), trichloroacetimidate, acyloxy, 2,2,2-trifluoroethanesulfonyl, imidazolesulfonyl, and 2,4,6-trichlorophenyl, with bromo being preferred. Protecting groups are known per se as chemical functional groups that can be selectively appended to and removed from functionalities, such as amine groups and thiol groups. These groups are present in a chemical compound to render such functionality inert to chemical reaction conditions to which the compound is exposed. See, e.g., Greene and Wuts, Protective Groups in Organic Synthesis, 2d edition, John Wiley & Sons, New York, 1991.

In embodiments wherein thiol-containing functionality is appended to 2'-O-, 3'-O-, or 5'-O-positions, amine functionality in the base portion of the nucleoside preferably next is protected under non-acidic conditions with protecting groups known in the art, including benzoyl and isobutyryl groups. Alternatively, base protection can precede reaction with thiol reagent $L_1$—$(CH_2)_n$—S—$R_{1a}$. Suitably protected nucleosides can be assembled into an oligonucleosides according to known techniques. See, e.g., Beaucage, et al., *Tetrahedron* 1992, 48, 2223.

Compounds according to the invention also can be prepared by reacting 5-halogen substituted pyrimidine nucleosides or 2- or 8-halogen substituted purine nucleosides with an acetylenic reagent having formula HC≡C—$CH_2$—Q—$R_3$ ($R_3$=protecting group) under conditions effective to couple the pyrimidine or purine base with the acetylenic reagent and form a nucleoside bearing a substituent having formula —C≡C—$CH_2$—Q—$R_3$ at the pyrimidine 5-position or at the purine 2- or 8-position. Numerous suitable protecting groups are known in the art, including, but not limited to: amine protecting groups such as trifluoroacetate (triflate), allyloxycarbonyl (Alloc), benzyloxycarbonyl (CBz), chlorobenzyloxycarbonyl, t-butyloxycarbonyl (Boc), fluorenylmethoxycarbonyl (Fmoc), isonicotinyloxycarbonyl (i-Noc) groups; hydroxyl protecting groups such as t-butyldiphenylsilyl, t-butyldimethylsilyl, and dimethoxytrityl groups; and thiol protecting groups such as S-trityl, S-p-methoxybenzylthioether, S-p-nitrobenzylthioether, and S-t-butylthioether. (see, e.g., Veber and Hirschmann, et al., *J. Org. Chem.* 1977, 42, 3286 and Atherton, et al., The Peptides, Gross and Meienhofer, Eds, Academic Press; New York, 1983; Vol. 9 pp. 1–38). Coupling preferably is mediated by a metal selected from palladium, nickel, platinum and iridium under conditions generally in accordance with Haralambidis, et al., *Nucleic Acids Research* 1987, 15, 4857. Once coupling is effected, the protecting group is removed and the resultant free hydroxy, thio, or amino compound is condensed with a suitable thiol derivative having formula $R_4$—$(CH_2)_n$—S—$R_{1a}$ where $R_4$ is $R_5$OOC—, HS, or —NCS where $R_5$ is H, chloro, alkyl having 1–3 carbon atoms, or active esters of carboxylic acids.

Compounds according to the invention also can be prepared by reacting metal-substituted pyrimidine nucleosides or purine nucleosides with an acrylate having formula $H_2C$=C—C(O)$OR_6$ ($R_6$=alkyl having 1–3 carbon atoms) under conditions effective to couple the pyrimidine or purine base with the acrylate and form a nucleoside bearing a substituent having formula —CH=CH—C(O)OH at the pyrimidine 5-position or at the purine 2- or 8-position. Coupling is effected under conditions generally in accordance with Dreyer, et al., *Proc. Natl. Acad. Sci. USA* 1985, 82, 968. Once coupling is effected, acid is condensed with an amino thiol derivative having formula $H_2N$—$(CH_2)_n$—S—$R_{1a}$.

Compounds according to the invention also can be prepared by reacting nucleosides bearing leaving groups, $L_2$, at 5-pyrimidine positions or at 2-, 6-, or 8-purine positions with, for example, aminothiol derivatives having formula HQ—$(CH_2)_n$—S—$R_{1a}$ under conditions effective to displace the leaving group. Such displacement preferably occurs at room temperature in solvents such as dimethylformamide (DMF) or dimethylsulfoxide (DMSO). Suitable leaving groups include halogen, alkylsulfonyl, substituted alkylsulfonyl, arylsulfonyl, substituted arylsulfonyl, hetercyclcosulfonyl, trichloroacetimidate, and pentafluorophenol.

Oligonucleosides according to the invention also can be prepared by assembling an oligonucleoside and appending thiol functionality thereto. For example, oligonucleosides having free hydroxyl groups can be assembled according to known techniques and then reacted with a reagent having formula $L_1$—$(CH_2)_n$—S—$R_{1a}$. As will be recognized, however, greater selectivity can be achieved in terms of placement of thiol functionality within an oligonucleoside by introducing such functionality, as discussed above, on selected nucleosides and then using both the selected nucleosides and other nucleosides to construct an oligonucleoside.

Thiol functionality also can be appended to phosphonate linkages (i.e., (5')-O—P(X)(H)—O-(3')) found within an oligonucleoside (see, e.g., Todd et al., *J. Chem. Soc.* 1966, 239; Frohler et al., *Nucleic Acids Res.* 1986, 14, 160; Letsinger, et al., *Proc. Natl. Acad. Sci. USA* 1989, 86, 6553) For example, oligonucleosides containing at least one phosphonate linkage can be reacted in the presence of base with a thiol reagent having formula HQ—$(CH_2)_n$—S—$R_{1a}$ under conditions effective form an internucleoside linkage having formula (5')-O—P[X][Q—$(CH_2)_n$—S—$R_{1a}$]—O-(3').

Thiol functionality also can be appended to amine-containing linkages (i.e., —$CH_2$—NH—O—$CH_2$—) found within an oligonucleosides. (see, e.g., U.S. patent applications Ser. Nos. 08/039,979 and 08/039,846, cited above). For example, oligonucleosides having at least one amine-containing linkage can be condensed a thiol reagent having formula HOC(O)—$(CH_2)_n$—S—$R_{1a}$ under conditions effective to form an internucleoside linkage having formula —$CH_2$—N[C(O)—$(CH_2)_n$—S—$R_{1a}$]—O—$CH_2$—.

Once assembled, an oligonucleoside bearing one or more groups having formula —$R_S$—S—$R_{1a}$ is treated with acid under conditions to remove protecting group $R_{1a}$. Representative acids include silver cation and mercuric cation. Once deprotected, the oligonucleoside can be contacted with a thiol-containing steroid molecule, reporter molecule, lipophilic molecule, reporter enzyme, peptide, or protein in the presence of a thiol-based coupling reagent. Useful coupling reagents include 2,2'-dithiobis(5-nitropyridine) and other pyridyl disulfides.

Alternatively, an oligonucleoside bearing one or more groups having formula —$R_S$—S—H can be contacted with electrophillic moieties having formula (maleimido)-$R_2$ or $L_3$—$CH_2C(O)$—$R_2$ where $L_3$ is a leaving group. As will be recognized, the sulfur atom on the oligonucleoside bonds with the former electrophillic moiety via 1,4-addition and with the latter via nucleophilic displacement. Preferred electrophillic moieties include phospholipid maleimide, o-phenanthroline-5-iodoacetamide, fluorescein maleimide, and pyrene maleimide (see, e.g., Example 22).

Thus, the invention first builds the desired linked nucleoside sequence in the normal manner on the DNA synthesizer. One or more (preferably two or more) of the linked nucleosides are then functionalized or derivatized with the lipophilic steroid, reporter molecule, lipophilic molecule, reporter enzyme, peptide or protein.

Additional objects, advantages, and novel features of this invention will become apparent to those skilled in the art upon examination of the following examples, which are not intended to be limiting. For example, thiol groups in addition to those having formula $—R_A—S—R_1$ (e.g., cysteine, glutathione, penicillamine, 2-pyridylmercaptyl, $Br—CH_2—CO—NH—CH_2—CH_2—STr$, $SH—C—(CH_3)_2CH_2—NH—CH_2—CH_2—NH—CH_2—C—(CH_3)_2SH$, $HOOC—CH_2—CH_2—S—S—CH_3OOCS$, $CH_3—CO—S—C(CH_3)—CH_2—C—NH—(CH_2)_2—COOH$) can be employed. (see, e.g., Dizio, et al., *Bioconjugate Chem.* 1991, 2, 353 and Greenfield, et al., *Bioconjugate Chem.* 1990, 1, 400) All oligonucleotide sequences are listed in a standard 5' to 3' order from left to right.

EXAMPLE 1

S-Trityl-6-mercaptohexylbromide,1,1',1"-{{(6-bromohexyl)thiol]methylidyne]trisbenzene (Compound 1)

To a solution of triphenylmethanethiol (Fluka; 69 g, 250 mmol) in 500 mL 95% ethanol (EtOH) was added 11 grams of sodium hydroxide dissolved in 75 mL of water (275 mmol). After stirring for about 15 minutes in argon atmosphere, using an addition funnel, 1,6-dibromohexane (91.5 g, 375 mmol, 58 mL) dissolved in 100 mL of 95% EtOH was added dropwise over a period of 1 hour with vigorous stirring. After about 15 minutes of stirring of addition, a brown white solid separates out from the reaction flask. After stirring for additional 4 hours, the reaction mixture was filtered. The filtrate was evaporated under high vacuum and the oily residue was combined with the filtered residue and dissolved in 500 mL $CH_2Cl_2$, filtered again, the filtrate was washed once with water (200 mL) and once with saturated NaCl solution. After drying the $CH_2Cl_2$ layer over $MgSO_4$, it was concentrated to 200 mL in volume. About 200 mL of hexane was added and the solution was left in freezer. Three crops of cream white product was isolated out. Total yield 81 g (184 mmol, 73% yield). After one more recrystallization the product melted at 91–92° C.

Portions of the product are independently treated with sodium cyanide followed by hydrolysis to give the corresponding acid, S-trityl-6-mercaptohexanoic acid (Compound 2), with lithium azide followed by triphenylphosphine reduction to give the corresponding amine, S-trityl-6-mercapto hexylamine (Compound 3), and with sodium hydrogen sulfide to give the corresponding thiol, (1-S-trityl-thio-hexylmercaptan) (Compound 4).

EXAMPLE 2

2'-O-[6-[(Triphenylmethyl)thio]hexyl]-adenosine and 3'-O-[6-[(triphenylmethyl)thio]hexyl]-adenosine (Compounds 5 and 6)

Adenosine (22.5 g) was alkylated with this S-trityl-6-mercaptohexylbromide (37.5 g) in the presence of DMF and sodium hydride to yield a 2'-O-(Compound 6) and 3'-O-alkylated (Compound 5) mixture in the ratio of 84:16 (as judged by $^{13}C$ NMR). The yield was 27%.

EXAMPLE 3

N-Benzoyl-2'-O-[6-[(triphenylmethyl)thio]hexyl]-adenosine (Compound 8) and N-benzoyl-3'-O-[6-[(triphenylmethyl)thio]hexyl]-adenosine (Compound 7)

To 16.5 grams of alkylation mixture (5 and 6, 26.4 mmols) in 260 mL of dry pyridine added 17 mL of chlorotrimethyl silane with external cooling with ice bath and stirring. After 30 minutes, 15.6 mL of benzoyl chloride (134.3 mmols) was added and the ice bath was removed. After 2 hours the reaction mixture was again cooled in an ice bath and 55 mL of ice-cold water was added. After 15 minutes of stirring, 55 mL of conc. $NH_4OH$ was added. After an additional 30 minutes the reaction mixture was evaporated to an oil on a rotoevaporator and dissolved in 300 mL $CH_2Cl_2$ and extracted with saturated $NaHCO_3$ solution (2×100 mL). The organic layer was dried and loaded into a silica gel (750 grams) and eluted with 7:3 ethyl acetate:hexane to give 18.3 g (25.10 mmol) of benzoylated 2' and 3' isomeric mixture (Compounds 7 and 8) 95.1% yield.

EXAMPLE 4

N-Benzoyl-5'-O-[Dimethoxytrityl]-2'-O-[6-[(triphenylmethyl)thio]hexyl]-adenosine (Compound 10) and N-Benzoyl-5'-O-[Dimethoxytrityl]-3'-O-[6-[(triphenylmethyl)thio]hexyl]-adenosine (Compound 9)

The base protected nucleoside mixture from the previous step was coevaporated with 2×100 mL of anhydrous pyridine. The resultant material was redissolved in 100 mL of anhydrous pyridine and with stirring, 13.9 g (41.0 mmol) dimethoxytritylchloride was added. The reaction mixture was stirred for 1.5 hours, after which thin layer chromatography (TLC; hexane:ethyl acetate (EtOAc), 1:1) showed disappearance of starting material. Methanol (20 mL) was added and the reaction was stirred for 30 minutes. Pyridine was evaporated and the residue was coevaporated once with 200 mL of toluene. The resultant residue was dissolved in 100 mL of $CH_2Cl_2$ and applied to a silica gel column (1000 g, packed in hexane). The column was eluted with the following solvents: 100% Hexane (1L); 45:55 EtOAc-hexane (3L) 50:50 EtOAc-hexane (3L) and 55:45 EtOAc-hexane until all 2'-O-isomer was eluted out. Then it was eluted with 60:40 EtOAc:Hexane 2 liter followed by 70:30 EtOAc:Hexane until all 3'-O-isomer is off the column. The isolated yields (56% combined yield) were: 10.3 g [2'-isomer (Compound 10)]; 2.4 g (3'-isomer) (Compound 9) and 1.9 g (2'+3' isomeric mixture). $R_f$=0.28 for 2'-isomer in hexane:EtOAc 1:1 and $R_f$=0.13 for 3'-isomer (Compound 9) in the same solvent system.

EXAMPLE 5

Adenosine-N-benzoyl-5'-O-[bis (4-methoxyphenyl-O-phenylmethyl]-2'-O-[6-[(triphenylmethyl)thio] hexyl]-3'-[2-cyanoethylbis(1-methylethyl) phosphoramidite]

The nucleoside N-benzoyl-5'-O-[Dimethoxytrityl]-2'-O-[6-[(triphenylmethyl) thio]hexyl]-adenosine (Compound 10; 4.6 g, 4.46 mMol) was dissolved in 60 mL $CH_2Cl_2$ anhydrous. Diisopropylamine tetrazolide salt (0.4 g, 2.23 mmol)

was added followed by phosphitylation reagent. The reaction mixture was stirred overnight. TLC analysis (1:1 EtOAc:Hexane) showed completion (>95%) of the reaction. Then the mixture was transferred into 100 mL of saturated NaHCO$_3$ in a separatory funnel. The reaction was washed with 100 mL CH$_2$Cl$_2$ containing 1% Et$_3$N. The organic layer was washed with 100 mL of saturated NaCl solution, dried over anhydrous sodium sulfate and evaporated to give 6.75 g of the crude product. It was then purified in a silica column (200 g, in a 25 cm×7.5 cm column) packed in 50:50 EtOAc:hexane containing 0.1% Et$_3$N. The column was eluted with the same solvent followed by 60:40 Et:OAc:hexane to give the product 11 as a colorless foam. (4.38 g, 3.6 mmol, 81% yield). $^{31}$P NMR (CDCl$_3$): 150.6, 151.4 ppm (d).

EXAMPLE 6

Controlled Pore Glass (CPG) Attached To Nucleoside 10 (Compound 17)

Succinylated CPG, prepared according to Damha, et al., *Nucleic Acids Res.* 1990, 18, 3813, (0.3 g, with a loading of approximately 80 micromoles/g, dried under vacuum for 3 hours immediately before use) was added to 3 ml anhydrous pyridine in a 50 ml round-bottom flask. 1-(3-Dimethylaminopropyl)-3-ethyl carbo-diimide (0.12 g, 0.63 mmol), triethylamine (25 ml, distilled over CaH$_2$), dimethylaminopryidine (0.005 g, 0.03 mmol) and nucleoside 10 (0.21 g, 0.203 mmol) were added under Ar and the mixture shaken mechanically for 19 hours. More nucleoside (0.025 g, 0.025 mmol) was added and the mixture shaken an additional 5.5 hours Pentachlorophenol (0.045 g, 0.17 mmol) was added and the mixture shaken 18 hours. CPG was filtered off and washed successively with dichloromethane, triethylamine, and dichloromethane. CPG was then dried under vacuum, suspended in 15 ml piperidine and shaken 30 min. The product, nucleoside-CPG (Compound 17), was filtered off, washed thoroughly with dichloromethane and again dried under vacuum. Extent of loading (determined by spectrophotometric assay of dimethoxytrityl cation in 0.3 M p-toluenesulfonic acid at 498 nm) was approximately 30 mmol/g.

EXAMPLE 7

Isolation Of Compounds 7 and 8

Compound 10 (0.50 g, 0.48 mmol) was dissolved. in dichloromethane. Acetic acid (80%) in water was added and the mixture stirred overnight. The solvents were evaporated in vacuo and the residue dissolved in dichloromethane and loaded onto a silica gel column. The resultant product 8 (290 mg, 83% yield, R$_f$=0.38 in 80% ethyl acetate in hexanes) was eluted with a gradient of 50% to 100% ethyl acetate in hexanes. Product was analyzed by $^1$H, $^{13}$C, and $^{13}$C-APT NMR and mass spectroscopy.

The corresponding 3'-isomer 9 was similarly deprotected and purified to yield the 5'-deprotected product 7 (220 mg, 63%, R$_f$=0.51). Product was analyzed by NMR and mass spectroscopy.

EXAMPLE 8

Isolation Of Compounds 5 and 6

Nucleoside 8 (200 mg, 0.27 mmol) was dissolved in 10 mL pyridine in a 500 mL pressure flask. Fresh ammonium hydroxide (125 mL) was added and the reaction mixture was heated at 55° in a water bath. After 3 days the mixture was cooled to 0°, transferred to a 500 mL round-bottom flask and the solvents removed in vacuo. The residue was dissolved in dichloromethane, extracted once with saturated NaHCO$_3$ and saturated NaCl and dried over MgSO$_4$. Solvent was removed in vacuo, the residue redissolved in a small amount of dichloromethane and applied to a silica gel column. Compound 6 (150 mg, 89%, R$_f$=0.50 in 100% ethyl acetate) was eluted with a gradient of 50% to 100% ethyl acetate in hexanes followed by 20% MeOH in ethyl acetate.

The corresponding 3'-isomer 7 was similarly deprotected and purified to yield product 5 (125 mg, 87% yield, R$_f$=0.43).

EXAMPLE 9

2'-O-[6-Thio hexyl]-adenosine (Compound 18) and 3'-O-[6-Thio hexyl]-adenosine (Compound 19)

Nucleoside 6 (130 mg, 0.19 mmol) is dissolved in 4 mL chloroform. Silver Nitrate (8 mM) in EtOH (12 mL) is added and the reaction mixture stirred for 45 minutes. Dithiothreitol (0.35 M) in chloroform (3 mL) is added and the reaction stirred overnight. The white precipitate is filtered off and. the solvent removed in vacuo. The residue is dissolved in dichloromethane, extracted once with saturated NaHCO$_3$ and saturated NaCl and dried over MgSO$_4$. The solvent is removed in vacuo. The product is purified on a silica gel column or by HPLC. The product (Compound 18) is analyzed by $^1$H, $^{13}$C, and $^{13}$C-APT NMR and mass spectroscopy. Similarly, nucleoside 5 (95 mg, 0.15 mmol) is deprotected and the product 19 purified and analyzed.

EXAMPLE 10

Attachment Of Thiol Linker At 5-Position Of Pyrimidines

A. 3',5'-di-toluyl-5-iododeoxyuridine is condensed with N-trifluoroacetyl-propargylamine in the presence of bis-(triphenylphosphine) palladium chloride and cuprous iodine (Haralambidis, et al., *Nucleic Acids Res.* 1987, 15, 4857). This nucleoside is then deprotected to give the free amine at 5 position which is condensed with HOOC—(CH$_2$)6-S-Tr, (Compound 2).

B. Preparation of 2'-deoxyuridine-5-(propionic acid methyl ester) is carried out according to the published procedure of Telser et al., *J. Am. Chem. Soc.* 1989, 111, 6966. Briefly, 5-chloro-mercury-2'-deoxyuridine is reacted with methyl acrylate under the conditions described by Dreyer, et al., *Proc. Natl. Acad. Sci. USA* 1985, 82, 968. The resultant 2'-deoxyuridine-5-(propenoic acid methyl ester) is reduced with hydrogen/palladium on carbon to yield 2'-deoxy uridine-5-(propionic acid methyl ester).

This compound is converted to the 5'-dimethoxytrityl derivative and then reacted with 1-S-trityl-hexyl-6-amine 3 by an ester-amide exchange reaction as described by Dreyer, et al. for other amines.

EXAMPLE 11

Attachment Of Thiol Linker At 2-Position Of Purines

2-Fluoro-2'-deoxyinosine is reacted with compound 3 following the conditions of Harris, et al., *J. Am. Chem. Soc.* 1991, 113, 4328. The resulting 2-position thiol linker placed nucleoside is further derivatized and incorporated into oligonucleotides.

EXAMPLE 12

Attachment Of Thiol Linker At 8-Position Of Purines

8-Bromoadenosine is reacted with the sodium salt of HS—$(CH_2)_6$—S-Tr. (Compound 4). The resulting 8-position modified nucleoside is then further modified and incorporated into oligonucleotides.

EXAMPLE 13

Preparation Of A Phosphonate Internucleotide Linkage And Attachment Of A Thiol Linker Thereto A fully protected oligonucleotide with an internucleotide H-phosphonate at a specific site synthesized following the protocol of Froehler, et al., *Nucleic Acids Research* 1986, 14, 160. This compound is oxidized with compound 4 in carbon tetrachloride-triethylamine medium to give the phosphorothioate triester O=P—S—$(CH_2)_6$—S-Tr. The oligonucleotide residue is further utilized for the full length oligonucleotide synthesis. The resultant oligonucleotide has the thiol linker attached to the backbone.

EXAMPLE 14

Preparation Of An Amine-containing Backbone And Attachment Of A Thiol Linker Thereto A dinucleoside protected dimer with either an 3'-$CH_2$—NH—O—$CH_2$-5' or 5'-$CH_2$—NH—O—$CH_2$-3' linkage is synthesized by the procedure of Vasseur, et al., *J. Am. Chem. Soc.* 1992, 114, 4006. This dimer is coupled with compound 2 using EDC and N-hydroxy succinimide. The coupled product has the configuration Tr-S—$(CH_2)_6$—C(O)—N—. The dimer is then 5'-dimethoxytritylated and 3'-phosphitylated and incorporated into full-length oligonucleotide synthesis.

EXAMPLE 15

Conversion Of Thiol 2'-O-hexyl Nucleoside Into Cholesterol Amidite

Nucleoside 10 (2 g) was dissolved in 40 mL of $CHCl_3$ containing 1 mL of triethylamine and treated with 8 mmol ethanolic silver nitrate (120 mL) at room temperature during which period the solution becomes turbid from clear. TLC (ethyl acetate:hexane 50:50) indicated a faster moving compound than the starting material and trityl on the top of the chromatograph. At this time 0.35 M solution of DTT in 40 mL of $CHCl_3$ was added and the resultant gelatinous precipitate was filtered over celite. The solution was dried and evaporated. The final TLC showed a slower moving spot than the starting material as expected out of a free thiol compound. It was used in the next step without any future purification.

2,2'-Dithiobis(5-nitropyridine) is treated with the thiol nucleoside in methylene chloride overnight. The precipitated 5-nitro pyridine-2-thione is removed by filtration, and the filtrate is concentrated. The resultant product 14 is treated with thiocholesterol in $CH_2Cl_2$ and shaken overnight to give the disulfide compound with the cholesterol. The cholesterol nucleoside is phosphitylated (compound 15) and used in oligonucleotide synthesis.

EXAMPLE 16

Conversion Of The Thiol Linker With A Trityl Protecting Group Into A Thiol Linker Protect By Disulfide Linkage Compound 14 is treated with propylmercaptan in $CH_2Cl_2$ and stirred overnight. The resulting disulfide compound (with —$(CH_2)_6$—S—S—$CH_2$—$CH_2$—$CH_3$ linkage) is further derivatized and incorporated into oligonucleotides. The free thiol group is liberated, before conjugation, by the addition of DTT.

EXAMPLE 17

Conversion To A Base Labile Thiol linker

The free nucleoside in the previous step (Compound 14) is treated with CBzCl (carbobenzyloxy chloride) in triethylamine. The thiol group is protected as a carbobenzyloxy ester group and phosphitylated and incorporated into oligonucleotides. Ammonia treatment for deprotection followed by DTT treatment yielded a free thio. containing oligonucleotide.

EXAMPLE 18

Oligonucleotide Synthesis

A 0.15 M solution of modified amidite (Compound 11) in anhydrous $CH_3CN$ was used in a 380B ABI DNA synthesizer to synthesize the following oligonucleotides:

d(GAA*CT) P=O (SEQ ID NO:1)

d(GAA*CT) P=S (SEQ ID NO:2)

wherein "*" denotes the thiol-modified nucleoside. Oligonucleotides with normal P=O backbones and modified P=S backbones were synthesized. The oligonucleotides containing P=S backbones were synthesized using the Beaucage reagent and standard synthesis cycles. During the phosphodiester synthesis, oxidation of the tervalent phosphorous was achieved using a 0.5 M solution of t-BuOOH in $CH_3CN$ since the tritylthioether group was sensitive to iodine/water solution. A coupling efficiency of greater than 90% was observed during the modified amidite coupling. For example, a 1 mmol synthesis of SEQ ID NO:1 yielded 36 OD units of purified oligonucleotide (72% overall isolated yield).

Both P=O and P=S oligonucleotides were dimethoxytrityl-on purified and the dimethoxytrityl group was removed with 15% acetic acid and then purified again. NMR analysis of SEQ ID NO:1 and SEQ ID NO:2 showed the integrity of these compounds. For SEQ ID NO:1, the trityl group resonance is observed between 7.0 and 7.5 ppm, and $^{31}P$ showed the expected 4 peaks. It is noteworthy that one of the signals is shifted about 0.5 ppm from the other signals as observed in other RNA/DNA hybrids. In the case of the phosphorothioate SEQ ID NO:2 a total of 64 signals is expected due to diastereomeric nature of chiral phosphorothioates; the multiplicity observed illustrates this fact. SEQ ID NO:1 was digested to individual nucleosides with snake venom phosphodiesterase and calf-intestinal alkaline phosphatase in order to confirm its nucleoside composition. Some resistance to enzymatic digestion (nuclease resistance) compared to unmodified oligonucleotides was observed which may be due to the presence of the 2'-O-tether.

Using the same amidite, the following antisense oligonucleotide sequences also were made: TGGGA*GCCATAGCGAGCC P=S (SEQ ID NO:3), ICAM antisense oligonucleotide with P=S backbone; TCTGAGTAGCAGAGGAGCTA*AG P=O (SEQ ID NO:4), sequence in the 5'-cap region of ICAM with P=O backbone.

SEQ ID NO:3 serves to evaluate the tritylthioether group in uptake experiments to determine its ability to inhibit ICAM (Intra Cellular Adhesion Molecules) protein expression. SEQ ID NO:4 is conjugated to O-phenanthroline and targeted against the 5'-cap-messenger RNA of ICAM system to cleave the target RNA.

EXAMPLE 19

Conjugation Reactions Of 2'-O-hexylthiol Linker

To illustrate the conjugation potential of the 2'-O-thiol tether, SEQ ID NO:1 was treated with 0.1M $AgNO_3$ in TEAA buffer followed by DTT treatment to generate a free thiol group. At this stage, it was reacted with four classes of compounds each having an either haloacetamide or a maleimide group and the desired functionality at the other end. The following compounds were employed: (1) a phospholipid maleimide, which can offer cell signalling and trafficking properties to nucleic acids; (2) 5-iodoacetamido-O-phenanthroline, which is a nucleic acid cleaving agent; this particular conjugation offers an added advantage of optimal placement for the cleaving agent as this reagent when complexed to cuprous ion reacts via a minor groove attack at the C-1' position; (3) pyrenemaleimide, which may stabilize the nucleic acid duplex via intercalation; and (4) fluorescein maleimide, which is used as a general diagnostic tool, serving to follow the uptake of antisense oligonucleotides. The conjugations were carried out in phosphate buffer (pH 8.0) and yields were greater than 95% (no starting oligonucleotide was apparent in the HPLC analysis). The conjugates were easily purified by size exclusion and reverse phase HPLC and characterized by their UV-VIS spectra (where applicable). The retention times of different oligonucleotides and their conjugates are given in Table I. Fluorescein maleimide, pyrene maleimide and phospholipid maleimide were purchased from Molecular Probes (Eugene, Oreg.). O-Phenanthroline-5-iodoacetamide was synthesized according to the published procedure of Sigman, *Biochemistry* 1990, 29, 9097.

TABLE I

HPLC retention times of SEQ ID NO: 1 and SEQ ID NO: 2 and their derivatives

| Entry | Oligonucleotide | Retention Time (mins) | Approximate % $CH_3CN$ needed for elution |
|---|---|---|---|
| 1 | d(GAUCT)[a] | 17.00 | 16 |
| 2 | DMTr-d(GAA*CT) | 46.18 | 45 |
| 3 | d(GAA*CT), I | 39.24 | 39 |
| 4 | I-phospholipid conjugate | 22.40 | 22 |
| 5 | I-o phenathroline conjugate | 26.30 | 26 |
| 6 | I-Fluorescein conjugate | 25.90 | 26 |
| 7 | I-Pyrene conjugate | 35.5 | 36 |
| 8 | DMTr-d(GAA*CT) P = S | 46.3 | 46 |

[a]A normal diester for comparison with entry 3.

HPLC conditions: C-18 column; linear 1% increase of $CH_3CN$ concentration for every minute.

EXAMPLE 20

5'-O-(S-Trityl-hexylthio)thymidine (Compound 20)

5'-Dimethoxytrityl thymidine is treated with 2 equivalents of benzyloxymethyl chloride in methylene chloride in the presence of excess of diisopropylethylamine. N-3,3'-O-dibenzyloxymethyl protected nucleoside is obtained and purified by silica column. 5'-Dimethoxytrityl group is then removed by treatment with 80% acetic acid and the product is treated with NaH in THF followed by adding compound 1. 5'-Alkylated compound is obtained and on hydrogenolysis the benzyloxymethyl groups are removed. The compound is then phosphitylated and used to synthesize oligonucleotides having a 5'-thiol linker built in the nucleoside.

EXAMPLE 21

Synthesis Of 3'-thiol Terminal Oligonucleotide Via 2'-O-(S-trityl Hexyl Mercaptan Linker) And 3'-O-(S-trityl-hexyl-mercaptan) Linker Compound 17 is used to synthesize an oligonucleotide with the following sequence, GCATA*, where modified adenosine is directly attached to CPG. The resultant oligonucleotide has a nucleotide with a thiol tether 2'-O—$(CH_2)_5$—S-Tr group at the 3'-end of the oligonucleotide.

Similarly, nucleoside 9 was attached to Control Pore Glass according to Example 6 and used for oligonucleotide synthesis. The product oligonucleotide has a nucleotide at the 3' terminal which has a 3'-O—$(CH_2)_6$—S-Tr group.

EXAMPLE 22

A. Determination Of Cellular Uptake And Activity Of Thiol Linker Containing Oligonucleotide.

This is determined by the inhibition of ICAM-1 utilizing the method of Chiang, et al., *J. Biol. Chem.* 1991, 266 18162.

ICAM-1 Assay: ICAM-1 expression on the cell surface was determined by ELISA using cells grown to confluence in 96-well plates. Cells were washed three times with Dulbecco's phosphate-buffered saline and fixed for 20 minutes in 2% formaldehyde diluted in Dulbecco's PBS. The cells were washed three times with Dulbecco's PBS, blocked for 1 hour at 37° C. with 2% bovine serum albumin in Dulbecco's PBS, and incubated with ICAM-1 monoclonal antibody 84H10 (0.5 µg/ml) for 1 hour at 37° C. Antibody bound to the cells was determined by incubation with a 1:1000 dilution of biotinylated goat anti-mouse IgG followed by incubation with a 1:1000 dilution of B-galactosidase-conjugated streptavidin. The plates were developed with 100 µl of 3.3 mM chlorophenolred-B-D-galactopyranoside in 50 mM sodium phosphate, 1.5 mM $MgCl2$, pH 7.0. Product formed was detected by absorbance at 575 nm. The data were expressed as percent control activity, which was calculated as described by Chiang, et al., in the above reference.

Oligonucleotide Treatment of Cells: Cells were washed three times with pti-MEM prewarmed to 37° C. Opti-MEM containing either 10 µg/ml DOTMA solution (HUVEC) or 20 mg/ml DOTMA solution (A549 cels) was added to each well of the plate (100 µl). Oligonucleotides were sterilized by centrifugation through 0.2 µM Centrex cellulose acetate filters. Oligonucleotides were added as 20×stock solution to the wells and incubated for 4 hours at 37° C. and then stimulated with the appropriate cytokine for 14–16 hours as indicated. ICAM-1 expression was determined as described above.

SEQ ID NO:3 is used in the above assay to assess its effect on ICAM expression. It is seen that the oligonucleotide effectively inhibits ICAM protein synthesis.

B. RNA Cleavage Assay Using Oligonucleotide Containing Thiol Linker.

SEQ ID NO:4 is thiol deprotected and conjugated to O-phenanthroline reagent. The conjugate is targeted against 5'-capped RNA of the ICAM system. The hybrid is incubated at 37° C. over a 48 hour period in the presence of excess Cu(II) salt under buffered conditions. Analysis of the reaction by gel electrophoresis (as described by Baker, *J.*

Am. Chem. Soc. 1993, 115, 3378) demonstrate that the oligonucleotide-O-phenanthroline-Cu complex cleave the target RNA strand.

EXAMPLE 23

Derivatized Linked Nucleosides, i.e. Oligonucleotides, Having Cross-linkable Thio Moieties An oligonucleotide of the sequence

A*TC GGC TTT TGC CGA* T SEQ. ID NO. 5 wherein * denotes an adenosine nucleotide modified to include a 2'-O-hexylthio linker was prepared in a 10 μMol scale using the procedure of Example 18. Compound 11 of Example 5 was used to introduce the modified adenosine nucleotide at the indicated positions. Oxidation was effected using t-BuOOH. The mercaptan groups of the modified nucleotides were protect via triphenylmethyl groups.

EXAMPLE 24

Derivatized Linked Nucleosides, i.e. Oligonucleotides, Cross-linked via Thio Derivatized Nucleosides to Form Hairpin Structure The oligonucleotide of Example 23 was cross-linked to form a hairpin structure utilizing 2'-O—(CH$_2$)$_6$—S—S—(CH$_2$)$_6$—O-2' linkages diagonally across the Watson-Crick (WC) based paired oligonucleotide. To effect crosslinking, 40 ods (optical density units) of the oligonucleotide of Example 23 was taken in 1 mL of 0.1M TEAA and 150 μL of 1M AgNO$_3$ was added. After 30 minutes 200 μL of 1M DTT solution was added, vortexed thoroughly and left aside for 10 minutes. The reaction mixture was then loaded into a previously prepared Sephadex G-25 column to remove the small molecule reagents. The fate of oligonucleotide was followed by reverse HPLC. A peak A corresponding to the starting oligonucleotide was identified. Due to the presence of two triphenylmethyl groups, peak A was very lipophilic and had a high retention time (approximately 37 mins). An earlier eluting peak (approximately 23 minutes), peak B, corresponded to the oligonucleotide having free —SH groups. A further peak, peak C, eluted at approximately 22 minutes from the sephadex column. Crosslinking of peak B to peak C is favored or triggered by the base pairs above and below the linkage. After about 1 hour, the peak B completely disappears to the product, peak C.

To confirm that peak C was the crosslinked product, pure C was treated with 1M DTT (5 ods in 0.5 mL) and analyzed for its reversal back to B. The crosslink seems to be a robust linkage presumably due to the WC base pairs. After 1 or 2 hrs, there was no reaction; however after standing overnight, C was converted back to an equilibrium mixture of B and C in which B predominates (>70%). After 24 hrs, C was completely convert back to B.

To further confirm the crosslinked structure, the product crosslinked oligonucleotide was melted in 10 mM NaCl. The observed "Tm" was >90° C. In higher salt concentrations the crosslinked hairpin oligonucleotide did not melt.

Disulfide crosslinked oligonucleotides prepared as per this example, have application as decoy oligonucleotides ("sense approach") to target nucleic acid binding sites of proteins and transcription factors. As such, these disulfide linkages are substrates for reductases in the biological systems. The released mercaptans can covalently link to cysteine residues of the target proteins and can cause permanent inactivation. In a similar approach, they can also be used to trap and study protein-antisense oligonucleotide complexes.

What is claimed is:

1. A compound comprising a plurality of linked nucleosides, wherein:

each nucleoside includes a ribofuranosyl sugar portion and a base portion; and at least one of said nucleosides bears at a 5-pyrimidine position or at a 2-, 6-, or 8-purine position a substituent having formula:

—Q—$R_A$—S—$R_1$;

or

—C≡C—$R_A$—Q—C(O)—$R_A$—S—$R_1$;

—CH=CH—C(O)—Q—$R_A$—S—$R_1$;

or

—CH=CH—$R_A$—Q—C(O)—Q—$R_A$—S—$R_1$;

where:

each $R_A$ is independently alkyl having from 1 to about 10 carbon atoms;

Q is NH, O, or S;

$R_1$ is H or a thiol protecting group or has formula S—$R_2$, $CH_2C(O)$—NH—$R_2$, $CH_2$—CH=CH—C(O)—$R_2$, —$CH_2$—$CH_2$—NH—$S(O)_2$—$R_2$, or (maleimido)-$R_2$; and $R_2$ comprises a steroid molecule, a reporter molecule, a lipophilic molecule, a reporter enzyme, a peptide, a protein, a reporter group, an alkylator, an intercalator, a cell receptor binding molecule, a crown ether, a crown amine, a porphyrin, a crosslinking agent, a peptide nucleic acid, or a thiol attached to a poly(ethylene glycol);

provided that a 6-purine substituent does not have formula —NH—$R_A$—S—$R_1$ when $R_1$ is H or a thiol protecting group.

2. The compound of claim 1 wherein more than one of said nucleosides bears said substituent at a 5-pyrimidine position or at a 2-, 6-, or 8-purine position.

3. The compound of claim 1 wherein $R_A$ is $(CH_2)_n$ where n is an integer from 1 to about 10.

4. The compound of claim 3 wherein n is 6.

5. The compound of claim 1 wherein $R_1$ is H or trityl.

6. The compound of claim 3 wherein said nucleoside bears at a 5-pyrimidine position a substituent having formula —C≡C—$CH_2$—NH—C(O)—$(CH_2)_n$—S—$R_1$.

7. The compound of claim 3 wherein said nucleoside bears at a 5-pyrimidine position a substituent having formula —CH=CH—C(O)—NH—$(CH_2)_n$—S—$R_1$.

8. The compound of claim 3 wherein said nucleoside bears at a 2- or 8-purine position a substituent having formula —NH—$(CH_2)_n$—S—$R_1$.

9. A compound comprising a plurality of linked nucleosides, wherein:

each nucleoside includes a ribofuranosyl sugar portion and a base portion; and at least two of said nucleosides are bound by a linkage having formula:

(5')-O—P[X][Q—$R_A$—S—$R_1$]—O -(3')

where:

X is O or S;

Q is NH, O, or S;

$R_A$ is alkyl having from 1 to about 10 carbon atoms;

$R_1$ is H or a thiol protecting group or has formula S—$R_2$, $CH_2C(O)$—NH—$R_2$, $CH_2$—CH=CH—C(O)—$R_2$, —$CH_2$—$CH_2$—NH—$S(O)_2$—$R_2$, or (maleimido)-$R_2$; and $R_2$ comprises a steroid molecule, a reporter molecule, a lipophilic molecule, a reporter enzyme, a peptide, a protein, a reporter group, an alkylator, an intercalator, a cell receptor binding molecule, a crown ether, a crown amine, a porphyrin, a crosslinking agent, a peptide nucleic acid, or a thiol attached to a poly(ethylene glycol);

provided that Q is not NH when $R_1$ is H or a thiol protecting group.

10. The compound of claim 9 wherein $R_A$ is $(CH_2)_n$ where n is an integer from 1 to about 10.

11. The compound of claim 10 wherein n is 6.

12. The compound of claim 10 wherein $R_1$ is H or trityl.

13. The compound of claim 10 wherein said nucleosides are bound by a linkage having formula —O—$CH_2$—P[O][S—$(CH_2)_n$—S—$R_1$]—O—.

* * * * *